US012807667B2

(12) United States Patent
Wang et al.

(10) Patent No.: US 12,807,667 B2
(45) Date of Patent: Nov. 24, 2026

(54) IL-7 FUSION PROTEIN AND RELATED METHODS

(71) Applicant: JECHO LABORATORIES, INC., Frederick, MD (US)

(72) Inventors: Shusheng Wang, Ellicott City, MD (US); Jianwei Zhu, Frederick, MD (US); Haiqiu Huang, North Bethesda, MD (US); Ailin Wang, Urbana, MD (US); Kaiyong Yang, Potomac, MD (US); Yueqing Xie, Clarksburg, MD (US); Hua Jiang, Clarksburg, MD (US)

(73) Assignee: JECHO LABORATORIES, INC., Frederick, MD (US)

( * ) Notice: Subject to any disclaimer, the term of this patent is extended or adjusted under 35 U.S.C. 154(b) by 607 days.

(21) Appl. No.: 18/254,223

(22) PCT Filed: Nov. 23, 2021

(86) PCT No.: PCT/US2021/060441

§ 371 (c)(1),
(2) Date: May 24, 2023

(87) PCT Pub. No.: WO2022/115396

PCT Pub. Date: Jun. 2, 2022

(65) Prior Publication Data

US 2024/0092851 A1 Mar. 21, 2024

Related U.S. Application Data

(60) Provisional application No. 63/129,817, filed on Dec. 23, 2020, provisional application No. 63/118,285, filed on Nov. 25, 2020.

(51) Int. Cl.
*C07K 14/54* (2006.01)
*A61P 37/04* (2006.01)
*C07K 14/765* (2006.01)
*A61K 38/00* (2006.01)

(52) U.S. Cl.
CPC .......... *C07K 14/5418* (2013.01); *A61P 37/04* (2018.01); *C07K 14/765* (2013.01); *A61K 38/00* (2013.01); *C07K 2319/02* (2013.01); *C07K 2319/31* (2013.01)

(58) Field of Classification Search
CPC .................................................. C07K 14/5418
See application file for complete search history.

(56) References Cited

U.S. PATENT DOCUMENTS

| | | | |
|---|---|---|---|
| 6,165,476 | A | 12/2000 | Strom et al. |
| 7,323,549 | B2 | 1/2008 | Lauder et al. |
| 7,708,985 | B2 | 5/2010 | Morre et al. |
| 8,338,675 | B1 | 12/2012 | Lauder et al. |
| 11,041,007 | B2 | 6/2021 | Yang et al. |
| 2005/0158832 | A1 | 7/2005 | Young et al. |
| 2005/0249701 | A1 | 11/2005 | Morre et al. |
| 2015/0030617 | A1 | 1/2015 | Jenkins et al. |
| 2020/0208133 | A1 | 7/2020 | Madison et al. |
| 2021/0113606 | A1 | 4/2021 | Sahin et al. |

FOREIGN PATENT DOCUMENTS

| | | |
|---|---|---|
| CN | 1898262 A | 1/2007 |
| EP | 3575319 | 12/2019 |
| KR | 20200120632 | 10/2020 |

OTHER PUBLICATIONS

Stratagene Catalog, 1988, p. 39.*
PCT International Search Report and Written Opinion for PCT Patent Application No. PCT/US2021/060441 mailed Mar. 15, 2022.
European Patent Office, Extended European Search Report, Application No. 21898993.7-111/4251186 PCT/US2021060441, dated Oct. 4, 2024, 10 pages.
Boudil, A., Matei, I.R., Shih, H.-Y., Bogdanoski, G., Yuan, U.S., Chang, S.G., Montpellier, B., Kowalski, P.E., Voisin, V., Bashir, S., Bader, G.D., Krangel, M.S., Guidos, C.J., 2015. IL-7 coordinates proliferation, differentiation and Tcra recombination during thymocyte β-selection. Nat Immunol 16, 397-405. https://doi.org/10.1038/ni.3122.
Brennan, S., 1996. All about albumin: Biochemistry, genetics and medical applications By Theodore Peters, Jr, Academic Press, 1996. US$85.00 (xx + 432 pages) ISBN 0 12 552110 3. Trends in Biochemical Sciences 21, 451-452. https://doi.org/10.1016/s0968-0004(96)80445-2.
Carter, D.C., Ho, J.X., 1994. Structure of Serum Albumin. Lipoproteins, Apolipoproteins, and Lipases 153-203. https://doi.org/10.1016/s0065-3233(08)60640-3.
Chia, J., Louber, J., Glauser, I., Taylor, S., Bass, G.T., Dower, S.K., Gleeson, P.A., Verhagen, A.M., 2018. Half-life-extended recombinant coagulation factor IX-albumin fusion protein is recycled via the FcRn-mediated pathway. J Biol Chem 293, 6363-6373. https://doi.org/10.1074/jbc.M117.817064.
Larsen, M.T., Kuhlmann, M., Hvam, M.L., Howard, K.A., 2016. Albumin-based drug delivery: harnessing nature to cure disease. Mol Cell Ther 4, 3-3. https://doi.org/10.1186/s40591-016-0048-8.
Mackall, C.L., Fry, T.J., Gress, R.E., 2011. Harnessing the biology of IL-7 for therapeutic application. Nat Rev Immunol 11, 330-342. https://doi.org/10.1038/nri2970.
Nilsen, J., Bern, M., Sand, K.M.K., Grevys, A., Dalhus, B., Sandlie, I., Andersen, J.T., 2018. Human and mouse albumin bind their respective neonatal Fc receptors differently. Sci Rep 8, 14648-14648. https://doi.org/10.1038/s41598-018-32817-0.
Sleep, D., Cameron, J., Evans, L.R., 2013. Albumin as a versatile platform for drug half-life extension. Biochimica et Biophysica Acta (BBA)—General Subjects 1830, 5526-5534. https://doi.org/10.1016/j.bbagen.2013.04.023.

(Continued)

*Primary Examiner* — Prema M Mertz
(74) *Attorney, Agent, or Firm* — McAndrews, Held & Malloy, Ltd.

(57) ABSTRACT

The disclosure provides IL-7 fusion proteins as well as compositions comprising them. The disclosure further provides methods of treating and/or preventing lymphopenia or immunodeficiency in a subject, wherein the method includes administering a fusion protein as described herein.

11 Claims, 5 Drawing Sheets

Specification includes a Sequence Listing.

(56) References Cited

OTHER PUBLICATIONS

Strohl, W.R., 2015. Fusion Proteins for Half-Life Extension of Biologics as a Strategy to Make Biobetters. BioDrugs 29, 215-239. https://doi.org/10.1007/s40259-015-0133-6.

Chen, D., Tang, T.-X., Deng, H., Yang, X.-P., Tang, Z.-H., 2021. Interleukin-7 Biology and Its Effects on Immune Cells: Mediator of Generation, Differentiation, Survival, and Homeostasis. Frontiers in Immunology 12.

Rothschild, M.A., Oratz, M., Schreiber, S.S., 1988. Serum albumin. Hepatology 8, 385-401. https://doi.org/10.1002/hep.1840080234.

Chinese Patent Office, Office Action for Chinese Application No. 202180078955.7 dated Mar. 18, 2026, 27 page.

* cited by examiner

IL-7 FUSION PROTEIN AND RELATED METHODS

CROSS REFERENCE TO RELATED APPLICATIONS

This application claims priority to U.S. Provisional Patent Application Ser. No. 63/118,285, filed Nov. 25, 2020, and to U.S. Provisional Patent Application Ser. No. 63/129,817, filed Dec. 23, 2020, both of which are incorporated herein by reference in their entirety.

INCORPORATION BY REFERENCE

This application incorporates by reference a Sequence Listing submitted with this application in computer readable form (CRF) as a text file entitled "64647WO01_SeqList".

BACKGROUND

Interleukin-7 (IL-7) is an immune modulator produced by stromal cells in lymphoid tissue. IL-7 is involved in lymphocyte homeostasis, specifically for the development of T cells and their maintenance and preservation in the periphery via interactions with its receptor, interleukin-7 receptor (IL-7R), which is expressed by cells of the lymphoid lineage. In the thymus, IL-7 directly stimulates recombination of the T-cell receptor γ-chain (TCRγ) locus to increase the antigen diversity of T cells. In circulating T cells, IL-7 induces expression or activity of anti-apoptotic factors and proliferation signals, as well as reduces apoptotic factors, resulting in T cell proliferation.

Its immunostimulatory effect makes IL-7 an attractive candidate therapeutic for immunodeficiency treatment and prevention, however, there is a need for strategies to extend the serum half-life of IL-7.

Among other aspects, described herein are novel IL-7 fusion proteins that extend the half-life of the IL-7 protein, and can be used in methods for treatment and prevention of immunodeficiency.

SUMMARY OF THE DISCLOSURE

The present disclosure generally provides an interleukin 7 (IL-7) fusion protein. In one aspect, the disclosure provides an IL-7 fusion protein that binds IL-7 receptor.

In some embodiments, a fusion protein comprises an IL-7 protein, an albumin protein, and a hinge region that joins the IL-7 protein and the albumin protein. In some aspects, the IL-7 protein is human IL-7 and the albumin protein is human serum albumin. In some embodiments, the human IL-7 comprises the amino acid sequence of SEQ ID NO: 15. In some embodiments, the human serum albumin (HSA) comprises the amino acid sequence of SEQ ID NO: 16. In some embodiments, the hinge region is human IgD. In some embodiments, the hinge region comprises the amino acid sequence of SEQ ID NO: 18. The IL-7 protein can be disposed toward the C-terminus of the fusion protein and the HSA disposed toward the N-terminus of the fusion protein. Alternatively, the HSA protein can be disposed toward the C-terminus of the fusion protein and the IL-7 protein disposed toward the N-terminus of the fusion protein.

In some embodiments, the fusion protein further comprises a signal peptide. The signal peptide can be a mouse IgG peptide. In some embodiments, the signal peptide comprises the amino acid sequence of SEQ ID NO: 17.

In some embodiments, the fusion protein comprises an amino acid sequence of SEQ ID NO: 19. On other embodiments, the fusion protein comprises an amino acid sequence of SEQ ID NO: 20.

The fusion proteins disclosed herein can extend the serum half-life of the IL-7 protein relative to recombinant or exogenous human IL-7 when administered to a subject. Various strategies can be used to extend protein serum half-life. For example, the fusion protein described here Human Serum Albumin (HSA)-IL7 comprises one, two, or three or more features. One feature comprises HSA as a fusion domain or fusion partner. HSA is the most abundant serum protein and has a serum-half life that is equivalent or better than IgG. Another feature comprises an IgD hinge region as the linker between domains (IL-7 and HSA). The IgD hinge is the longest hinge region among all immunoglobin and confers flexibility, allowing IL-7 to maintain its activity in the fusion format. A third feature is that IL-7 is linked to the C terminus of the HSA. This format provides the better biochemical and biophysical properties when compared to an N terminal location for the fusion to IL-7.

In any of the aspects and embodiments described herein, the IL-7 fusion proteins disclosed herein can be used to treat and/or prevent lymphopenia in a subject. In some aspects, the IL-7 fusion proteins can stimulate white blood cell proliferation, lymphocyte proliferation, and/or lymphocyte differentiation in a subject. In other aspects, the IL-7 fusion proteins can treat and/or prevent immunodeficiency in a subject. Subjects that can benefit from the disclosed IL-7 fusion proteins include, without limitation, those having cancer, human immunodeficiency virus, hepatitis B, hepatitis C, lymphopenia, sepsis, and subjects having undergone stem cell, tissue, or organ transplantation. In certain aspects, the IL-7 fusion protein can increase white blood cells counts, increase lymphocyte counts, and/or increase T cell subpopulations, such as $CD3^+CD4^+$ T cells, CD3+$CD4^+$ T cells, and $CD3^+$ T cells in a subject. The methods disclosed herein comprise administering an IL-7 fusion protein to a subject.

Additional aspects of the disclosure will be apparent to one of ordinary skill in the art in view of the following description and illustrative examples.

DETAILED DESCRIPTION

Figure 1A:
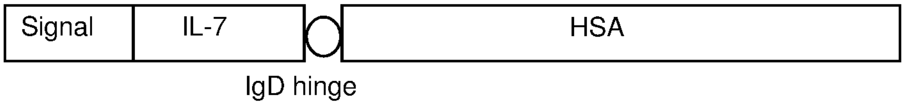
FIG. 1A illustrates an embodiment of an IL-7 fusion protein.

Before continuing to describe the present disclosure in further detail, it is to be understood that this disclosure is not limited to specific proteins, nucleic acids, compositions, or process steps, as such can vary while still falling within the scope of the description provided herein. It must be noted that, as used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

A. Fusion Proteins

As used herein, the term “fusion protein” refers to a polypeptide construct generated through the joining and expression of two or more genes encoding distinct polypeptides. The translation of the fusion gene results in a single polypeptide with functional properties derived from each of the original polypeptides. The polypeptides can be fused directly or joined via a linker or hinge.

Described herein are novel IL-7 fusion proteins. As used herein, the term “interleukin-7” or “IL-7” refers to IL-7 polypeptides or derivatives thereof having substantial amino acid sequence identify to a mature, wild-type mammalian IL-7 For example, IL-7 can refer to an amino acid sequence of a recombinant or non-recombinant polypeptide having an amino acid sequence of: i) a native allelic variant of an IL-7 polypeptide, ii) a biologically active fragment of an IL-7 polypeptide, or iii) a biologically active variant or analog of an IL-7 polypeptide. The IL-7 of the fusion protein can be obtained from any mammalian species, or obtained from a recombinant expression system (e.g., yeast, bacteria, etc.). The IL-7 may be glycosylated, partially glycosylated, or non-glycosylated.

In one aspect, an IL-7 fusion protein comprises IL-7, a hinge region, and an albumin protein, such as but not limited to, human serum albumin (HSA). In some embodiments, the IL-7 fusion proteins comprise less than the full-translated sequence of HSA. The IL-7 fusion protein can further comprise a signal peptide at the N-terminus of the fusion protein, which may be processed (e.g., cleaved) when the fusion protein is expressed or produced in certain host cells (e.g., mammalian host cells such as 293F or CHO-K1). In some embodiments, the IL-7 polypeptide of the fusion protein is human IL-7.

Figure 1B:
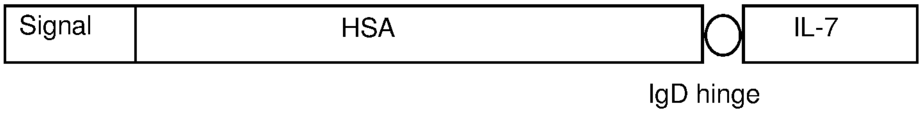
FIG. 1B illustrates another embodiment of an IL-7 fusion protein.

In one aspect, the IL-7 is disposed toward the N-terminus of the fusion protein and the HSA is disposed toward the C-terminus, with the hinge region disposed there between (FIG. 1A). In another aspect, the IL-7 is disposed toward the C-terminus of the fusion protein and the HSA is disposed toward the N-terminus with the hinge region disposed there between (FIG. 1B).

As used herein, the term “human serum albumin” refers to a HSA polypeptide or derivative thereof having substantial amino acid sequence identify to mature, wild-type human HSA, which is can be used as carrier protein at least because of its long serum half-life of up to 21 days. Other carrier proteins, aside from HSA, are also contemplated. In some aspects, the carrier protein is a heavy chain immunoglobulin constant domain derived from IgA, IgD, IgE, IgG, or IgM. In other aspects and embodiments, IL-7 can be modified by pegylation.

Fusion proteins of the disclosure are joined by the fusion of the C-terminal region (e.g., C-terminus) of one polypeptide or protein (IL-7 or HSA) to the N-terminal region (e.g., N-terminus) of a hinge or linker peptide and the fusion of the N-terminal region (e.g., N-terminus) of a second polypeptide or protein (IL-7 or HSA) to the C-terminal region (e.g., C-terminus) of the $1^{st}$ protein-hinge or linker complex. The hinge or linker peptide comprises an amino acid sequence that provides a covalent linkage between the protein domains (IL-7 and HSA), and can be immediately C-terminal to the last amino acid of the IL-7 or HSA. The hinge or linker region can be any peptide linker that is generally known and used in the art to generate fusion proteins. In some embodiments the hinge or linker is derived from the hinge region of an immunoglobulin such as, for example, an IgA, IgD, IgE, IgG, or IgM amino acid sequence. As used herein, “hinge region” refers to a polypeptide comprising an amino acid sequence that shares sequence identify or similarity with a portion of an immunoglobulin hinge region sequence. Accordingly, a “hinge region” encompasses fragments of the immunoglobulin hinge region that allow the linked polypeptides to achieve a biologically active conformation. Hinge regions in some example embodiments of the present disclosure share at least 70-80% sequence identify to a wild-type immunoglobulin hinge region amino acid sequence, preferably, greater than about 90% sequence identify. In some particular aspects, the hinge region comprises a hinge region from, or derived from, human IgD or IgG. Human IgD, which lacks cysteine and is the longest immunoglobulin hinge, provides increased fusion protein flexibility. Such flexibility can increase engagement or binding of the IL-7 fusion protein with the IL-7 receptor.

As used herein, “signal peptide” refers to a 5-30 amino acid peptide present at the N-terminus of the fusion protein. In some aspects, the fusion protein comprises an N-terminal signal peptide derived from an immunoglobulin amino acid sequence. In certain aspects, the signal peptide can be a mouse IgG peptide, specifically a mouse IgG kappa light chain, which lends to efficient expression and secretion of the fusion protein.

In some aspects, the fusion proteins disclosed herein can be characterized by one or more of the following structural and/or functional properties:

a. an amino acid sequence comprising: (i) human IL-7 (hIL-7) of SEQ ID NO: 15, (ii) human serum albumin (HSA) of SEQ ID NO: 16, (iii) a signal peptide of SEQ ID NO: 17, and (iv) a hinge peptide of SEQ ID NO: 18;
b. an amino acid sequence comprising: (i) human IL-7 (hIL-7) of SEQ ID NO: 15, (ii) human serum albumin (HSA) of SEQ ID NO: 16, and (iii) a hinge peptide of SEQ ID NO: 18;
c. binding specificity for IL-7 receptor;
d. an extended half-life relative to recombinant IL-7 in human serum;
e. an EC50 having a potency within 5-fold of recombinant IL-7 (e.g., 5× more or less potent);
f. the ability to extend the serum half-life of the IL-7 protein relative to recombinant or exogenous IL-7 proteins when administered to a subject;
g. the ability to stimulate white blood cell proliferation, lymphocyte proliferation, and/or lymphocyte differentiation; and
h. the ability to treat, attenuate, or reduce in severity lymphopenia or immunodeficiency in a subject.

In some aspects, an IL-7 fusion protein comprises an IL-7 protein having SEQ ID NO: 15.

In some aspects, an IL-7 fusion protein comprises HSA having SEQ ID NO: 16.

In some aspects, an IL-7 fusion protein comprises a hinge region having SEQ ID NO: 18.

In some aspects, an IL-7 fusion protein comprises a signal peptide having SEQ ID NO: 17.

In some aspects, an IL-7 fusion protein comprises human IL-7 (hIL-7) of SEQ ID NO: 15, HSA of SEQ ID NO: 16, a signal peptide of SEQ ID NO: 17, and a hinge peptide of SEQ ID NO: 18.

In some aspects, an IL-7 fusion protein comprises human IL-7 (hIL-7) of SEQ ID NO: 15, HSA of SEQ ID NO: 16, and a hinge peptide of SEQ ID NO: 18.

In some aspects, an IL-7 fusion protein comprises SEQ ID NO: 19.

In some aspects, an IL-7 fusion protein comprises SEQ ID NO: 20.

In still further aspects, the disclosure provides JL18008-1 and JL18008-2.

In some aspects, a fusion protein comprises an IL-7 protein having SEQ ID NO: 15.

In some aspects, a fusion protein comprises HSA having SEQ ID NO: 16.

In some aspects, a fusion protein comprises a hinge region having SEQ ID NO: 18.

In some aspects, a fusion protein comprises a signal peptide having SEQ ID NO: 17.

In some aspects, a fusion protein comprises human IL-7 (hIL-7) of SEQ ID NO: 15, HSA of SEQ ID NO: 16, a signal peptide of SEQ ID NO: 17, and a hinge peptide of SEQ ID NO: 18.

In some aspects, a fusion protein comprises human IL-7 (hIL-7) of SEQ ID NO: 15, HSA of SEQ ID NO: 16, and a hinge peptide of SEQ ID NO: 18.

In some aspects, a fusion protein comprises SEQ ID NO: 19.

In some aspects, a fusion protein comprises SEQ ID NO: 20.

As one of ordinary skill can appreciate, the sequences disclosed herein can be modified to some degree without compromising the ability of the fusion protein to interact with a target cell receptor, i.e., IL-7 receptor. In some aspects, fusion protein sequence variants retain the ability to stimulate white blood cell proliferation, lymphocyte proliferation, and/or lymphocyte differentiation in vivo and/or in vitro. In some aspects, fusion protein sequence variants retain the ability to treat, attenuate, or reduce in severity lymphopenia or immunodeficiency in a subject.

As used herein, sequence "variants" refer to a fusion protein amino acid sequence comprising at least one amino acid insertion, deletion, and/or substitution, wherein the resulting fusion protein maintains one or more of its functional characteristics as described herein. An amino acid insertion variant is characterized by the insertion of one or more amino acids between two existing amino acids. An amino acid deletion variant is characterized by the deletion of one or more amino acids from the fusion protein sequence. An amino acid substitution is characterized by at least one amino acid in the sequence being replaced by another amino acid. In embodiments relating to substitutions, the amino acid substitution(s) may be a conservative substitution, (i.e. an amino acid from one family of amino acids (acidic, basic, non-polar, and uncharged, based on side chain characteristics, including size) is substituted with an amino acid from the same family).

In some aspects, the sequence identity between the variant fusion protein sequence and the fusion protein sequences disclosed herein will be at least 85%, 86%, 87%, 88%, 89%, 90%, 91%, 92%, 93%, 94%, 95%, 96%, 97%, 98%, or 99%. "Sequence identity" refers to the percentage of amino acid residues that are identical to the sequences being compared.

B. Labels, Conjugates, and Moieties

The fusion proteins disclosed herein can be conjugated to a therapeutic agent, solid support, affinity agent, or a detectable agent. Fusion proteins of the disclosure can be conjugated to labels wherein the fusion protein and/or its associated targets(s) can be detected. Labels include, without limitation, a chromophore, a fluorophore, a fluorescent protein, a phosphorescent dye, a tandem dye, a particle, a hapten, an enzyme and a radioisotope.

In certain aspects, the fusion proteins are conjugated to a fluorophore. The choice of the fluorophore attached to the fusion protein will determine the absorption and fluorescence emission properties of the conjugated fusion protein. Physical properties of a fluorophore label can include, but are not limited to, spectral characteristics (absorption, emission and stokes shift), fluorescence intensity, lifetime, polarization and photo-bleaching rate, or combination thereof. All of these physical properties can be used to distinguish one fluorophore from another, and thereby allow for multiplexed analysis. Other desirable properties of the fluorescent label can include cell permeability and low toxicity, for example if labeling of the fusion protein is to be performed in a cell or an organism (e.g., a living animal).

In certain aspects, the conjugated label can comprise an enzyme. Enzymes are desirable labels in some embodiments because amplification of the detectable signal can be obtained and result in increased assay sensitivity. The enzyme itself does not produce a detectable response but functions to break down a substrate when it is contacted by an appropriate substrate such that the converted substrate produces a fluorescent, colorimetric or luminescent signal. Enzymes can amplify the detectable signal because one enzyme on a labeling reagent can result in multiple substrates being converted to a detectable signal. The enzyme substrate is selected to yield the preferred measurable product, e.g. colorimetric, fluorescent or chemiluminescence. Such substrates are extensively used in the art and are well known by one skilled in the art and include for example, oxidoreductases such as horseradish peroxidase and a substrate such as 3,3'-diaminobenzidine (DAB); phosphatase enzymes such as an acid phosphatase, alkaline and a substrate such as 5-bromo-6-chloro-3-indolyl phosphate (BCIP); glycosidases, such as beta-galactosidase, beta-glucuronidase or beta-glucosidase and a substrate such as 5-bromo-4-chloro-3-indolyl beta-D-galactopyranoside (X-gal); additional enzymes include hydrolases such as cholinesterases and peptidases, oxidases such as glucose oxidase and cytochrome oxidases, and reductases for which suitable substrates are known.

Enzymes and their appropriate substrates that produce chemiluminescence are suitable for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another aspect, haptens, such as biotin, are also utilized as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

Enzymes and their appropriate substrates that produce chemiluminescence are suitable for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful.

In another aspect, haptens, such as biotin, are also utilized as labels. Biotin is useful because it can function in an enzyme system to further amplify the detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, nucleotides and the like.

In certain aspects, fluorescent proteins can be conjugated to the fusion protein as a label. Examples of fluorescent proteins include green fluorescent protein (GFP) and the phycobiliproteins and derivatives thereof. The fluorescent proteins, especially phycobiliprotein, are particularly useful for creating tandem dye labeled labeling reagents. These tandem dyes comprise a fluorescent protein and a fluorophore for the purposes of obtaining a larger stokes shift wherein the emission spectra is farther shifted from the wavelength of the fluorescent protein's absorption spectra.

In certain aspects, the label is a radioactive isotope. Examples of suitable radioactive materials include, but are not limited to, iodine ($^{121}$I, $^{123}$I, $^{125}$I, $^{131}$I) carbon ($^{14}$C), sulfur ($^{35}$S), tritium ($^{3}$H), indium ($^{111}$In, $^{112}$In, $^{113}$mIn, $^{115}$mIn), technetium ($^{99}$Tc, $^{99}$mTc), thallium ($^{201}$Ti), gallium $^{67}$Ga), palladium ($^{103}$Pd), molybdenum ($^{99}$Mo), xenon ($^{135}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, and $^{97}$Ru.

In some aspects, drugs (e.g., other active agents) can be conjugated to the fusion protein. For example, a fusion protein can be conjugated to a therapeutic moiety or agent, such as an immunotherapy drug. In some embodiments, the fusion protein can bind to a target cell, and deliver the immunotherapy drug to the cell. Any immunotherapeutic known in the art can be conjugated to the fusion protein. In certain embodiments, drugs and other molecules can be conjugated to a fusion protein via site-specific conjugation. Non-limiting example embodiments of such additional active agents can include antiviral agents, antibiotic agents, antifungal agents, antiparasitic agents, gamma globulin, and the like. Similarly, the fusion protein disclosed herein may be used in combination with one or more other therapeutic interventions that may be used in the treatment of conditions such as lymphopenia and/or immunodeficiency in a subject.

C. Polynucleotides Encoding Fusion Proteins & Recombinant Cells Producing Fusion Proteins The disclosure provides methods for producing fusion proteins. In certain aspects, the disclosure provides for recombinant methods of generating a fusion protein. In some embodiments, recombinant nucleic acids encoding for the fusion protein can be operably linked to one or more regulatory nucleotide sequences in an expression construct. In some embodiments, the nucleic acid sequences encoding the signal peptide, first or second polypeptide sequences, or the linker/hinge region can be cloned in the same expression vector in a defined orientation or can be cloned in different vectors. If expression is carried out using one vector, the coding genes can have their own genetic elements (e.g., promoter, RBS, leader, stop, polyA, etc.) or they can be cloned with one single set of genetic elements, but connected with a cistron element. Regulatory nucleotide sequences can be appropriate for a host cell used for expression. Numerous types of appropriate expression vectors and suitable regulatory sequences are known in the art for a variety of host cells. Typically, one or more regulatory nucleotide sequences can include, but are not limited to, promoter sequences, leader or signal sequences, ribosomal binding sites, transcriptional start and termination sequences, translational start and termination sequences, and enhancer or activator sequences. Any known constitutive or inducible promoter are contemplated for use with the aspects and embodiments included in the disclosure. The promoters can be either naturally occurring promoters, or hybrid promoters that combine elements of more than one promoter. An expression construct can be present in a cell on an episome, such as a plasmid, or the expression construct can be inserted in a chromosome.

In certain aspects, an expression vector contains a selectable marker gene to allow the selection of transformed host cells. Selectable marker genes are known and can vary with the host cell used. In certain aspects, the disclosure relates to an expression vector comprising a nucleotide sequence encoding a polypeptide that is operably linked to at least one regulatory sequence. Regulatory sequences are generally known and can be selected to direct expression of the encoded polypeptide. Accordingly, the term regulatory sequence includes promoters, enhancers, and other expression control elements. Exemplary, non-limiting regulatory sequences are described in Goeddel; Gene Expression Technology: Methods in Enzymology, Academic Press, San Diego, CA (1990). It should be understood that the design of the expression vector can depend on such factors as the choice of the host cell to be transformed and/or the type of protein (e.g., fusion protein) to be expressed. Moreover, the vector's copy number, the ability to control that copy number and the expression of any other protein encoded by the vector, such as antibiotic markers, can be considered.

In some embodiments relating to methods of producing a fusion protein, a host cell can be transfected with one or more expression vector(s) encoding a fusion protein, and can be cultured under appropriate conditions to allow expression of the polypeptide(s) to occur. The fusion protein can be secreted and isolated from cells and/or cell culture media containing the fusion protein. Alternatively, the fusion protein can be retained in the cytoplasm or in a membrane fraction and the cells harvested and lysed, and the fusion protein subsequently purified and isolated. A cell culture includes host cells, media and other byproducts. Any suitable media for cell culture can be used in methods of production. Fusion proteins can be isolated from cell culture medium, host cells, or both using common techniques for purifying proteins, including, for example, ion-exchange chromatography, gel filtration chromatography, ultrafiltration, electrophoresis, and immunoaffinity purification. In certain aspects, the fusion protein can be produced with a domain (e.g., a His-tag) that facilitates its purification.

A recombinant nucleic acid can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*. In certain aspects, mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press, 1989) Chapters 16 and 17. In some instances, it can be desirable to express the recombinant polypeptide(s) by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the ß-gal containing pBlueBac III).

Techniques for making fusion genes are well known. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another aspect, the fusion gene can be synthesized by conventional techniques including automated DNA synthesizers. Alternatively, PCR amplification of gene fragments can be carried out using anchor primers which give rise to complementary overhangs between two consecutive nucleic acid fragments which can subsequently be annealed to generate a chimeric gene sequence (see, for example, Current Protocols in Molecular Biology, eds. Ausubel et al., John Wiley & Sons: 1992).

In some aspects, an expression vector expressing any of the nucleic acids described above can be used to express a fusion protein in a host cell. For example, a fusion protein can be expressed in bacterial cells such as *E. coli*, insect cells (e.g., using a baculovirus expression system), yeast, or mammalian cells. Other suitable host cells are known to those skilled in the art.

Once the expression vector is transferred to a host cell by conventional techniques, the transfected cells are then cultured by conventional techniques to produce a fusion protein. Thus, the disclosure includes host cells containing a polynucleotide encoding a fusion protein, operably linked to a heterologous promoter. In certain aspects, if the fusion protein is encoded from different vectors, the vectors can be co-expressed in the host cell for expression of the entire fusion protein. In certain aspects, the fusion protein is expressed from a single promoter. In certain aspects, the fusion protein is expressed from multiple promoters. In certain aspects, the fusion protein is encoded on a single vector. In certain aspects, the fusion protein is encoded on multiple vectors.

Mammalian cell lines available as hosts for expression of fusion proteins are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), human epithelial kidney 293 cells, and a number of other cell lines. Different host cells have characteristic and specific mechanisms for the post-translational processing and modification of proteins and gene products. Appropriate cell lines or host systems can be chosen to ensure the correct modification and processing of the fusion protein or portion thereof expressed. To this end, eukaryotic host cells that possess the cellular machinery for proper processing of the primary transcript, glycosylation, and phosphorylation of the gene product can be used. Such mammalian host cells include but are not limited to CHO, HEK293, VERY, BHK, Hela, COS, MDCK, 293, 3T3, W138, BT483, Hs578T, HTB2, BT2O and T47D, NS0 (a murine myeloma cell line that does not endogenously produce any functional immunoglobulin chains), SP20, CRL7O3O and HsS78Bst cells.

In certain aspects, fusion proteins of the disclosure are stably expressed in a cell line. Stable expression can be used for long-term, high-yield production of recombinant proteins. For example, cell lines that stably express the fusion protein can be generated. Host cells can be transformed with an appropriately engineered vector comprising expression control elements (e.g., promoter, enhancer, transcription terminators, polyadenylation sites, etc.), and a selectable marker gene. Following the introduction of the foreign DNA, cells can be allowed to grow for 1-2 days in an enriched media, and then are switched to a selective media. The selectable marker in the recombinant plasmid confers resistance to the selection and allows cells that stably integrated the plasmid into their chromosomes to grow and form foci, which in turn can be cloned and expanded into cell lines. Methods for producing stable cell lines with a high yield are well known in the art and reagents are generally available commercially.

In certain aspects, fusion proteins of the disclosure are transiently expressed in a cell line. Transient transfection is a process in which the nucleic acid introduced into a cell does not integrate into the genome or chromosomal DNA of that cell, but is maintained as an extrachromosomal element, e.g. as an episome, in the cell. Transcription processes of the nucleic acid of the episome are not affected and a protein encoded by the nucleic acid of the episome is produced.

The cell line, either stable or transiently transfected, is maintained in cell culture medium and conditions well known in the art that result in the expression and production of fusion protein. In certain aspects, the mammalian cell culture media is based on commercially available media formulations, including, for example, DMEM or Ham's F12. In other aspects, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium can be optimized for a specific cell culture use, including, for example, cell culture growth medium that is formulated to promote cellular growth or cell culture production medium which is formulated to promote recombinant protein production. The terms "nutrient", "ingredient", and "component" are used interchangeably herein to refer to the constituents that make up a cell culture medium.

Once a fusion protein has been produced, it can be purified by any method known in the art for purification of a protein complex, for example, by chromatography (e.g., ion exchange, affinity, and size column chromatography), centrifugation, differential solubility, or by any other standard technique for the purification of proteins.

When using recombinant techniques, the fusion protein can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, supernatants from such expression systems are generally first concentrated using a commercially available protein concentration filter, for example, an Amicon or Millipore Pellicon ultrafiltration unit. A protease inhibitor such as PMSF can be included in any of the foregoing steps to inhibit proteolysis and antibiotics can be included to prevent the growth of adventitious contaminants.

The composition prepared from the cells can be purified using, for example, hydroxylapatite chromatography, hydrophobic interaction chromatography, ion exchange chromatography, gel electrophoresis, dialysis, and/or affinity chromatography either alone or in combination with other purification steps. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin, SEPHAROSE chromatography on an anion or cation exchange resin (such as a polyaspartic acid column), chromatofocusing, SDS-PAGE, and ammonium sulfate precipitation are also available.

Regardless of how a fusion protein is purified, to confirm functional binding activity, binding assays can be performed (before and/or after purification). For example, ELISA assays, including dual ELISA assays can be used. In some aspects, a first binding target is coated on a well, and binding to this target immobilizes the fusion protein. A tagged second binding target is added to the well, and detected. Only fusion proteins that are both immobilized via binding to the first binding target and bound to the second binding target will be detected.

In some aspects, the disclosure provides for recombinant cell lines expressing the fusion protein that can be deposited and maintained with an international depository institution that is authorized under the provisions of the Budapest Treaty (i.e., an International Depositary Authority, IDA).

D. Pharmaceutical Formulations

In certain aspects, the disclosure provides pharmaceutical compositions. Such pharmaceutical compositions can also be compositions comprising a fusion protein as disclosed herein and a pharmaceutically acceptable excipient. In certain aspects, the pharmaceutical compositions of the disclosure are used as a medicament (i.e., in methods of treating or preventing a disease or condition (e.g., lymphopenia), in a subject in need of treatment or preventative treatment). In some embodiments, pharmaceutical compositions can be compositions comprising a nucleic acid molecule that encodes a fusion protein as disclosed herein.

In certain aspects, a fusion protein (or a polynucleotide encoding the fusion protein) can be formulated with a pharmaceutically acceptable carrier, excipient or stabilizer, as pharmaceutical compositions. In certain aspects, such pharmaceutical compositions are suitable for administration to a human, or a non-human mammal or animal, via any one or more route of administration using methods known in the art. The route and/or mode of administration will vary depending upon the desired results. The term "pharmaceutically acceptable carrier" means one or more non-toxic materials that do not interfere with the effectiveness of the biological activity of the active ingredients. Such preparations can routinely contain salts, buffering agents, preservatives, compatible carriers, and optionally other therapeutic agents. Such pharmaceutically acceptable preparations can also contain compatible solid or liquid fillers, diluents or encapsulating substances, which are suitable for administration into a human. Other contemplated carriers, excipients, and/or additives, which can be utilized in the formulations described herein include, for example, flavoring agents, antimicrobial agents, sweeteners, antioxidants, antistatic agents, lipids, protein excipients such as serum albumin, gelatin, casein, salt-forming counterions such as sodium and the like. These and additional known pharmaceutical carriers, excipients and/or additives suitable for use in the formulations described herein are known in the art, e.g., as listed in "Remington: The Science & Practice of Pharmacy", $21^{st}$ ed., Lippincott Williams & Wilkins, (2005), and in the "Physician's Desk Reference", $60^{th}$ ed., Medical Economics, Montvale, N.J. (2005). Pharmaceutically acceptable carriers can be selected that are suitable for the mode of administration, solubility and/or stability desired or required.

The formulations described herein comprise active agents (i.e., one or more fusion proteins as disclosed herein) in a concentration resulting in a w/v appropriate for a desired dose. In certain aspects, the active agent is present in a formulation at a concentration of about 1 mg/ml to about 200 mg/ml, about 1 mg/ml to about 100 mg/ml, about 1 mg/ml to about 50 mg/ml, or about 1 mg/ml to about 25 mg/ml. In certain aspects, the concentration of the active agent in a formulation can vary from about 0.1% to about 75% by total weight. In certain aspects, the concentration of the active agent is in the range of 0.003 to 1.0 molar.

When used for in vivo administration, the formulations should be sterile. Formulations can be sterilized by various sterilization methods, including sterile filtration, radiation, etc. In one aspect, the formulation is filter-sterilized with a presterilized 0.22-micron filter. Sterile compositions for injection can be formulated according to conventional pharmaceutical practice as described in "Remington: The Science & Practice of Pharmacy", $21^{st}$ ed., Lippincott Williams & Wilkins, (2005).

Therapeutic compositions are encompassed by the pharmaceutical formulations described herein, and can formulated for particular routes of administration, such as oral, nasal, pulmonary, topical (including buccal and sublingual), rectal, vaginal and/or parenteral administration. The phrases "parenteral administration" and "administered parenterally"

as used herein refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The formulations can be in unit dosage form and prepared by any known method. Actual dosage levels of the active ingredients in the pharmaceutical compositions can be varied to obtain an amount of the active ingredient that is effective to achieve the desired therapeutic response for a particular patient, composition, and mode of administration, without being toxic to the patient (e.g., "a therapeutically effective amount"). The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. Suitable dosages can range from about 0.0001 to about 100 mg/kg of body weight or greater, for example about 0.1, 1, 10, or 50 mg/kg of body weight, with about 1 to about 10 mg/kg of body weight being suitable.

In some embodiments of the disclosure, the formulations can be suitable for research use. The concentration of active agent in such formulations, as well as the presence or absence of excipients and/or pyrogens, can be modified or selected based on the particular application and intended use.

The fusion proteins described herein can be used in methods that prevent, treat, or mitigate lymphopenia or immunodeficiency in a subject. As used herein, "lymphopenia", "lymphocytic leukopenia", or "lymphocytopenia" refer to a condition characterized by a reduced number of lymphocytes (i.e. T lymphocytes (aka T cells), B lymphocytes (aka B cells), and/or natural killer cells (aka NK cells)) in a subject's blood. As used herein, "immunodeficiency" and "immunodeficient" refer to a physiological state in which a subject's immune system is compromised in such a way that prevents an adequate immune response to fight infection and disease. In some aspects, immunodeficiency increases the subject's susceptibility to microbial infection (e.g. bacterial, viral, fungal, or protozoan infection).

In some aspects, lymphopenia in an adult subject is characterized by a lymphocyte count of less than 1,000-1,500 lymphocytes/uL blood. In some aspects, lymphopenia in a pediatric or adolescent subject is characterized by a lymphocyte count of less than 3,000 lymphocytes/uL blood. Assays to measure lymphocyte counts are known in the art and include complete blood count (CBC), flow cytometry, mitogen- and antigen-induced lymphocyte proliferation assays and ELISA. In some aspects, the fusion proteins of the disclosure can be used to increase white blood counts, increase lymphocyte counts, and/or increase T cell subpopulations in a subject in need thereof. In other aspects, the fusion proteins can be used to protect an immunocompromised subject or a subject at risk of becoming immunocompromised from developing lymphopenia or immunodeficiency. As used herein, "immunocompromised" refers to a subject having a weakened immune system or a reduced ability to fight infections or other diseases, due to a genetic disorder or disease, an infection, an environmental disorder or disease, or other environmental factors. Such methods can be carried out by administering to the patient a therapeutically effective dose of the fusion protein of the disclosure, or pharmaceutical compositions comprising such fusion proteins.

In some aspects, the disclosure relates to methods of treating or preventing lymphopenia or immunodeficiency in a subject having a disease or condition including, without limitation, cancer, human immunodeficiency virus (HIV), hepatitis B, hepatitis C, sepsis, aplastic anemia, lymphoma, an inherited immune disorder, tuberculosis, renal failure, autoimmune disorders such as lupus, rheumatoid arthritis, and myasthenia gravis, and heart failure. Methods of treatment and/or prevention of lymphopenia or immunodeficiency also include subjects receiving chemotherapy, radiation treatment, steroids, aderenocorticotropic hormone, and/or immunosuppressive medications as well as those having undergone stem cell, tissue, and/or organ transplantation.

As used herein, the term "disease" refers to any pathological state resulting in lymphopenia or immunodeficiency or a pathological state that may increase a subject's susceptibility to developing lymphopenia or immunodeficiency.

As used herein, lymphopenia or immunodeficiency can be determined or identified based on any available and/or accepted test to diagnose such conditions, including clinical presentation (i.e. analysis of physical signs or symptoms), blood count, and/or measurement of lymphocyte subpopulations and immunoglobulin levels. In some aspects, lymphopenia in a subject can be asymptomatic. In other aspects, symptoms of lymphopenia can include absent or diminished tonsils or lymph nodes, skin abnormalities (e.g. alopecia, eczema, pyoderma, and telangiectasia), evidence of hematologic disorder (e.g. pallor, petechiae, jaundice, and mouth ulcers), lymphadenopathy, splenomegaly, and recurring infection.

As used herein, "treat", "treating", or "treatment" refer to administering a fusion protein or composition as described herein to a subject in order to eliminate, reduce, or attenuate the clinical symptoms of lymphopenia or immunodeficiency; arrest, inhibit, reverse, or slow the progression of lymphopenia or immunodeficiency in a subject; prevent, reverse, or slow the loss of lymphocyte counts in the blood of a subject; stimulate the recovery of lymphocyte counts in the blood of a subject; stimulate the proliferation and/or differentiation of lymphocytes in a subject; and/or stimulate the proliferation and/or differentiation of white blood cells in a subject.

In some aspects, the disclosure provides methods for preventing lymphopenia or immunodeficiency in a subject. In some further aspects of the methods relating to preventing disease, the subject can be at risk for developing lymphopenia or immunodeficiency. By "being at risk" or having an "increased risk", a subject is identified as having a higher than normal chance of developing lymphopenia or immunodeficiency as compared to the general population. In some embodiments, a subject who has had, or who currently has cancer, HIV, hepatitis B, hepatitis C, sepsis, aplastic anemia, lymphoma, an inherited immune disorder, tuberculosis, renal failure, autoimmune disorders such as lupus, rheumatoid arthritis, and myasthenia gravis, heart failure, or is otherwise considered susceptible to being or becoming immunocompromised has an increased risk of developing lymphopenia or immunodeficiency. At risk subjects can also include subjects receiving chemotherapy, radiation treatment, steroids, aderenocorticotropic hormone, and/or immunosuppressive medications as well as those having undergone stem cell, tissue, and/or organ transplantation.

The term "immunotherapy" relates to a treatment involving a specific immune response, specifically, stimulation or recovery of immune cell populations. In the context of the present disclosure, terms such as "protect", "prevent", "prophylactic", "preventative", or "protective" relate to the prevention of the occurrence of or the exacerbation of lymphopenia or immunodeficiency in a subject. Persons having lymphopenia or immunodeficiency, immunocompromised persons, or persons at risk of developing lymphopenia, immunodeficiency, or becoming immunocompromised, as described above, would be considered candidates for immunotherapy.

A prophylactic administration of an immunotherapy, for example, a prophylactic administration of a fusion protein or a composition comprising a fusion protein as disclosed herein, can in certain embodiments protect the recipient from developing lymphopenia or immunodeficiency. In some embodiments, prophylactic administration can reduce the severity of lymphopenia or immunodeficiency.

A therapeutic administration of an immunotherapy, for example, a therapeutic administration of a fusion protein or a composition comprising a fusion protein as disclosed herein, can inhibit or attenuate the progression of lymphopenia, arrest or recover loss of white blood cell and/or lymphocyte counts, and/or inhibit, reduce, arrest, or alleviate clinical symptoms of lymphopenia.

The terms "subject", "individual", or "patient" are interchangeable, and relate to vertebrates, preferably mammals. For example, mammals in the context of the disclosure are humans, non-human primates, domesticated animals such as dogs, cats, sheep, cattle, goats, pigs, horses etc., laboratory animals such as mice, rats, rabbits, guinea pigs, etc., as well as animals in captivity such as animals in zoos. The term "animal" as used herein also includes humans. The term "subject" can also include a patient, i.e., an animal, an in particular embodiments, a human having lymphopenia, immunodeficiency, or an immunocompromised person.

The fusion proteins and compositions described herein can be administered via any conventional route, including by injection or infusion. In some embodiments, the administration can be carried out, for example, orally, intravenously, intraperitonealy, intramuscularly, subcutaneously, or transdermally.

The fusion proteins and the compositions comprising them are administered in effective amounts. An "effective amount" includes an amount that achieves a desired reaction or a desired effect and can be in the form of a single dose or as multiple doses. In the case of treatment of lymphopenia or immunodeficiency, the desired reaction relates to inhibition or attenuation of lymphopenia; recovery, interruption, or prevention of further loss of immune cell populations (e.g. white blood cells and lymphocytes); and/or alleviation or attenuation of clinical symptoms. A desired reaction can also be delay of onset or prevention of onset of lymphopenia or immunodeficiency.

An effective amount of a composition of the disclosure will depend on the severity of lymphopenia or immunodeficiency, underlying cause (i.e. disease or condition) of lymphopenia or immunodeficiency, the individual parameters of the patient, including age, physiological condition, size and weight, the duration of treatment, the type of an accompanying therapy (if present), the specific route of administration and similar factors. Accordingly, the doses of the compositions of the disclosure administered can depend on various combinations of such parameters. In embodiments in which an initial amount administered to a patient is insufficient, further administration with higher amounts, more frequent doses, or a different/more localized route of administration can be used.

In the methods and compositions disclosed herein, an IL-7 fusion protein can be administered to a subject to extend the serum half-life of the IL-7 protein relative to recombinant or exogenous IL-7. In certain embodiments, the half-life of the IL-7 protein is extended by at least 2 hours, more preferably by at least 4 hours when administered to a subject.

In some embodiments, when a subject is administered a fusion protein in a range of 50-150 μg/kg, the serum half-life of the human IL-7 is about 190-230 minutes, more preferably 190-330 minutes, relative to recombinant or exogenous IL-7.

In some embodiments, the IL-7 half-life extension of fusion proteins as described herein is sufficient to stimulate white blood cell proliferation, lymphocyte proliferation, and/or lymphocyte differentiation in a subject.

In certain embodiments, the IL-7 half-life extension of fusion proteins as described herein is sufficient to stimulate an increase in lymphocyte counts, specifically T cell counts, and more specifically T cell subpopulations including $CD3^+$ $CD4^+$ T cells, $CD3^+CD4^+$ T cells, and $CD3^+$ T cells.

Recovery or stimulation of lymphocyte populations can be facilitated by binding of the fusion protein with the IL-7 receptor of target immune cells.

F. Kits

Another aspect of the present disclosure is a kit. In one aspect, a kit comprises any of the compositions or pharmaceutical compositions of a nucleic acid, polypeptide, expression vector, or host cell described above, and instructions or a label directing appropriate use or administration. Optionally, a kit can also include one or more containers and/or a syringe or other device to facilitate delivery or use. The disclosure contemplates that all or any subset of the components for conducting research assays and/or for administering therapeutically effective amounts of a fusion protein can be enclosed in the kit. Similarly, the kit can include instructions for making a polypeptide by, for example culturing a host cell that expresses a nucleic acid that encodes a fusion protein of the disclosure under suitable conditions. By way of additional example, a kit for therapeutic administration of a fusion protein of the disclosure can comprise a solution containing a pharmaceutical formulation of the fusion protein, or a lyophilized preparation of the fusion protein, and instructions for administering the composition to a patient in need thereof and/or for reconstituting the lyophilized product.

The present disclosure also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient, e.g., an above-described fusion protein, is sterile and suitable for administration as a particulate free solution. In certain aspects, the formulation is suitable for intravenous administration, such as for intravenous infusion to a human or animal.

In a specific aspect, the formulations of the disclosure are formulated in single dose vials as a sterile liquid. Exemplary containers include, but are not limited to, vials, bottles, pre-filled syringes, IV bags, and blister packs (comprising one or more pills). Optionally associated with such container(s) can be a notice in the form prescribed by a governmental agency regulating the manufacture, use or sale of pharmaceuticals or biological products, which notice reflects approval by the agency of manufacture, use or sale for human diagnosis and/or administration.

As with any pharmaceutical product, the packaging material and container are designed to protect the stability of the product during storage and shipment. Further, the products of the disclosure include instructions for use or other informational material that advise the physician, technician, or patient on how to appropriately prevent or treat the disease or disorder in question. In other words, the article of manufacture includes instruction means indicating or suggesting a dosing regimen including, but not limited to, actual doses, monitoring procedures, etc., and other monitoring information.

A kit for research purposes can comprise a solution containing a fusion protein or a lyophilized preparation of a fusion protein of the disclosure, wherein the fusion protein binds specifically to one or more targets. The fusion protein can be labeled according to methods known in the art and described herein, including but not limited to labels such as small molecule fluorescent tags, proteins such as biotin, GFP or other fluorescent proteins, or epitope sequences such as his or myc. Similarly, primary antibodies used for detecting the fusion protein can be included in the kit. Primary antibodies can be directed to sequences on the fusion protein or to labels, tags, or epitopes with which the fusion protein is labeled. Primary antibodies can, in turn, be labeled for detection, or, if further amplification of the signal is desired, the primary antibodies can be detected by secondary antibodies, which can also be included in the kit. In some aspects, kits for research use can resemble kits intended therapeutic uses but further include a label specifying that the kit and its use is restricted to research purposes only.

G. Modification and/or Engineering

The disclosed fusion proteins can also be used to produce therapeutic immunoconjugates, wherein the fusion protein is conjugated with one or more therapeutic agents. For example, fusion proteins as described herein can be used in the production of protein-drug conjugates. Drugs that can be used include, without limitation, large and small molecule active agents such as, for example, immune system modulators, growth factors, (e.g., colony-stimulating factors (CSFs)), antiviral agents, antibiotic agents, antifungal agents, antiparasitic agents, and gamma globulin, and the like.

EXAMPLES

Example 1: Amplification of IL-7 Fusion Proteins

Tables 1 and 2 detail source DNA and primers for Polymerase Chain Reaction (PCR) amplification of exemplary human IL-7 (hIL-7), HSA, signal peptide, and hinge peptide in accordance with example embodiments as disclosed herein.

TABLE 1

Source DNA for Representative hIL-7, HSA, Signal Peptide, and Hinge Peptide

| DNA | Source (UniProt Knowledgebase ID) |
|---|---|
| Human IL-7 | P13232 |
| HSA | P02768 |
| Mouse IgG kappa light chain (signal peptide) | GenBank: AAH80787.1 |
| Human IgD (hinge peptide) | P0DOX3 |

TABLE 2

PCR Primers for Amplification of Representative hIL-7, HSA, Signal Peptide, and Hinge Peptide

| Target | Primers |
|---|---|
| Human IL-7 (JL18008-1) | 5' GTGCCTGGCAGCACCGGAGATTGTGATATTGAGGGC 3' (SEQ ID NO: 1)<br>5' GCCTGGGCCTTTGGGGACTCGTGTTCCTTTGTGCCCATC 3' (SEQ ID NO: 2) |
| Human IL-7 (JL18008-2) | 5' AGAGAGACCAAGACACCAGATTGTGATATTGAGGGCA 3' (SEQ ID NO: 3)<br>5' ACGGGCCCTCTAGACTCGAGTCATCAGTGTTCCTTTGTGCCCATCAG 3' (SEQ ID NO: 4) |
| HSA (JL18008-1) | 5' AGAGAGACCAAGACACCAGATGCTCACAAGTCTGAGG 3' (SEQ ID NO: 5)<br>5' ACGGGCCCTCTAGACTCGAGTCATCACAGGCCCAGGGCAGCCTG 3' (SEQ ID NO: 6) |
| HSA (JL18008-2) | 5' GTGCCTGGCAGCACCGGAGATGCTCACAAGTCTGAG 3' (SEQ ID NO: 7)<br>5' GCCTGGGCCTTTGGGGACTCCAGGCCCAGGGCAGCCTG 3' (SEQ ID NO: 8) |
| Mouse IgG kappa light chain (signal peptide) | 5' CGTTTAAACTTAAGCTTGGTACCGAGC 3' (SEQ ID NO: 9)<br>5' TCCGGTGCTGCCAGGCACCC 3' (SEQ ID NO: 10) |

TABLE 2-continued

PCR Primers for Amplification of Representative hIL-7, HSA, Signal Peptide, and Hinge Peptide

| Target | Primers |
|---|---|
| Human IgD (hinge peptide) | 5' GAGTCCCCAAAGGCCCAGGC 3' (SEQ ID NO: 11)<br>5' TGGTGTCTTGGTCTCTCTCTC 3' (SEQ ID NO: 12) |

PCR may be performed according to typical protocols, and may include or be adapted from the following strategy. HSA-IL7 is assembled by overlapping PCR techniques from four DNA fragments that encode for mouse IgG kappa light chain signal peptide, human HSA, the IgD hinge, and human interleukin-7. The individual DNA fragments corresponding to each of the above-mentioned genes are amplified by PCR in a 50 ul reaction prepared by mixing 2.5 ul of 10 uM forward primer, 2.5 ul 10 uM reverse primer, 1 ul diluted DNA template, 19 ul deionized water, 25 ul Q5 High Fidelity 2× Master Mix (M0492, NEB). The reaction is performed by preheating at 98° C. for 30 seconds, then 25 cycles of denaturation at 98° C. for 10 seconds, annealing at 65° C. for 30 seconds, and extension at 72° C. for 60 seconds. The PCR products are separated on a 1.2% agarose gel and are purified using gel DNA extraction kit (D4002, Zymo Research). A 2-step assembly protocol is used by assembling the signal peptide with HSA and the hinge peptide with IL-7, respectively, in a first step. The resulting PCR products are further assembled to give rise to the HSA-IL7 fusion gene. The assembly reaction comprises the pre-assembly reaction and the amplification reaction. The pre-assembly reaction is set up in a 30 ul reaction by mixing the two purified PCR products with 15 ul Q5 High Fidelity 2× Master Mix, and by running between 98° C. (10 sec) and 68° C. (80 sec) for 7 cycles. The amplification reaction is set up by adding 3 ul 10 uM forward primer, 3 ul 10 uM reverse primer, 9 ul dH2O, and 15 ul Q5 High Fidelity 2× Master Mix to the 30 ul pre-assembly reaction. The reaction utilizes a regular PCR protocol with preheating at 98° C. for 30 seconds and with 30 cycles of denaturation at 98° C. for 10 seconds, annealing at 55° C. for 30 seconds, and extension at 72° C. for 90 seconds. The final PCR product is digested by HindIII and XbaI, and is subcloned into the mammalian expression vectors pJL115 under a human pEF1 promoter. The coding region is confirmed by DNA sequencing (Genewiz). The human EF1 promoter from pEFlalpha-IRES containing a single point mutation (T578C) is amplified using the following primers: pCDNA3.1 hEF1a F1 5' CGCGCGACGCGTGGCTCCGGTGCCCGTCA 3' (SEQ ID NO: 13) pCDNA3.1 hEF1a R1 5' CTACTAGCTAGCTCACGACACCTGAAATGGAAGAAA 3' (SEQ ID NO: 14). Amplification reactions are performed with NEB Q5 2× Master Mix. The purified PCR products and pCDNA3.1(+) vector are digested with MluI at 37° C. for 1.5 hours. The PCR product(s) and vector are further digested with NheI at 37° C. for 1.5 hours. Ligation of the digested products is performed using T4 DNA ligase with an insert:vector molar ratio of 3:1. Ligation is carried out at 25° C. for 1 hour.

Example 2: Transfection and Cell Line Generation

Cell lines are generated via transfection of CHO K1 cells (ATCC) with a plasmid carrying a JL18008-1 or JL18008-2 expression cassette. Plasmid DNA is linearized by ScaI (NEB, Cat #R3122S), purified by Phase Lock gel (5Prime, Cat #2302830), and transfected using Freestyle Max (Gibco, Cat #94764) according to manufacturer's instruction. After transfection, the bulk pools and mini pools are generated from $0.5\times10^6$ cells and 5000 cells, respectively, in the presence of 12.5 μM MSX. The recovered pools are assessed using IL-7 ELISA kit (PEPROTECH Human IL-7 Standard ABTS ELISA Development Kit, Cat #900-K17) and top mini pools are subjected to two rounds of FACS cloning. FACS sortings are performed by staining cells with FITC-conjugated anti-HSA antibody made in house using a labeling kit (Sigma, Cat #FITC-1KT). 960 clones are deposited into 96-well plates and grown in CD CHO medium containing 1×HT supplement (Gibco, Cat #11067-030) and ClonaCell-CHO ACF Supplement (Stemcell, Cat #03820). After recovery from selection, top clones are gradually scaled up to shake flask. The titer is determined by Octet measurement using SAX sensors coated with CaptureSelect Biotin Anti-HSA Conjugate (Thermo Fisher, Cat #7102972100). Single-cell clones are generated by limiting-dilution cloning.

Transfected cells are cultured for 7-14 days to produce conditioned media. Conditioned media is collected and treated by centrifugation and/or filtration to remove cellular debris. JL18008-1 and JL18008-2 fusion proteins are isolated and purified from the conditioned media by a series of column chromatography, ultra filtration, and diafiltration. Column chromatography is performed using Capto Blue (GE Healthcare), Toyopearl Phenyl-650M (Tosoh Bioscience), Capto G HP (GE Healthcare), Capto SP ImpRes (GE Healthcare), and/or CaptureSelect (Thermo Fisher).

Tables 3 and 4 detail sequence information for exemplary IL-7 fusion proteins in accordance with example embodiments.

TABLE 3

Amino Acid Sequences for Representative Protein and Peptide Sequences

| Protein/Peptide | Sequence |
|---|---|
| human IL-7 | DCDIEGKDGKQYESVLMVSIDQLLDSMKEIGSNCLNN EFNFFKRHICDANKEGMFLFRAARKLRQFLKMNSTG DFDLHLLKVSEGTTILLNCTGQVKGRKPAALGEAQPT KSLEENKSLKEQKKLNDLCFLKRLLQEIKTCWNKILM GTKEH (SEQ ID NO: 15) |

TABLE 3-continued

Amino Acid Sequences for Representative Protein and Peptide Sequences

| Protein/Peptide | Sequence |
|---|---|
| Human Serum Albumin (HSA) | DAHKSEVAHRFKDLGEENFKALVLIAFAQYLQQCPFE<br>DHVKLVNEVTEFAKTCVADESAENCDKSLHTLFGDK<br>LCTVATLRETYGEMADCCAKQEPERNECFLQHKDDN<br>PNLPRLVRPEVDVMCTAFHDNEETFLKKYLYEIARRH<br>PYFYAPELLFFAKRYKAAFTECCQAADKAACLLPKLD<br>ELRDEGKASSAKQRLKCASLQKFGERAFKAWAVARL<br>SQRFPKAEFAEVSKLVTDLTKVHTECCHGDLLECADD<br>RADLAKYICENQDSISSKLKECCEKPLLEKSHCIAEVE<br>NDEMPADLPSLAADFVESKDVCKNYAEAKDVFLGMF<br>LYEYARRHPDYSVVLLLRLAKTYETTLEKCCAAADPH<br>ECYAKVFDEFKPLVEEPQNLIKQNCELFEQLGEYKFQN<br>ALLVRYTKKVPQVSTPTLVEVSRNLGKVGSKCCKHPE<br>AKRMPCAEDYLSVVLNQLCVLHEKTPVSDRVTKCCT<br>ESLVNRRPCFSALEVDETYVPKEFNAETFTFHADICTL<br>SEKERQIKKQTALVELVKHKPKATKEQLKAVMDDFA<br>AFVEKCCKADDKETCFAEEGKKLVAASQAALGL<br>(SEQ ID NO: 16) |
| Mouse IgG kappa light chain (signal peptide) | METDTLLLWVLLLWVPGSTG (SEQ ID NO: 17) |
| Human IgD (hinge peptide) | ESPKAQASSVPTAQPQAEGSLAKATTAPATTRNTGRG<br>GEEKKKEKEKEEQEERETKTP (SEQ ID NO: 18) |

TABLE 4

Amino Acid Sequences for Representative IL-7 Fusion Proteins

| IL-7 Fusion Protein (Internal Reference) | Sequence |
|---|---|
| JL18008-1 (IL7-HSA) | METDTLLLWVLLLWVPGSTGDCDIEGKDGKQYESVL<br>MVSIDQLLDSMKEIGSNCLNNEFNFFKRHICDANKE<br>GMFLFRAARKLRQFLKMNSTGDFDLHLLKVSEGTTIL<br>LNCTGQVKGRKPAALGEAQPTKSLEENKSLKEQKKL<br>NDLCFLKRLLQEIKTCWNKILMGTKEHESPKAQASS<br>VPTAQPQAEGSLAKATTAPATTRNTGRGGEEKKKE<br>KEKEEQEERETKTPDAHKSEVAHRFKDLGEENFKAL<br>VLIAFAQYLQQCPFEDHVKLVNEVTEFAKTCVADES<br>AENCDKSLHTLFGDKLCTVATLRETYGEMADCCAKQ<br>EPERNECFLQHKDDNPNLPRLVRPEVDVMCTAFHD<br>NEETFLKKYLYEIARRHPYFYAPELLFFAKRYKAAFTE<br>CCQAADKAACLLPKLDELRDEGKASSAKQRLKCASL<br>QKFGERAFKAWAVARLSQRFPKAEFAEVSKLVTDL<br>TKVHTECCHGDLLECADDRADLAKYICENQDSISSK<br>LKECCEKPLLEKSHCIAEVENDEMPADLPSLAADFV<br>ESKDVCKNYAEAKDVFLGMFLYEYARRHPDYSVVL<br>LLRLAKTYETTLEKCCAAADPHECYAKVFDEFKPLVE<br>NLIKQNCELFEQLGEYKFQNALLVRYTKKVPQVSTP<br>TLVEVSRNLGKVGSKCCKHPEAKRMPCAEDYLSVV<br>LNQLCVLHEKTPVSDRVTKCCTESLVNRRPCFSALE<br>VDETYVPKEFNAETFTFHADICTLSEKERQIKKQTA<br>LVELVKHKPKATKEQLKAVMDDFAAFVEKCCKADD<br>KETCFAEEGKKLVAASQAALGL (SEQ ID NO: 19) |
| JL18008-2 (HSA-IL7) | METDTLLLWVLLLWVPGSTGDAHKSEVAHRFKDLGEEN<br>FKALVLIAFAQYLQQCPFEDHVKLVNEVTEFAKTCVADES<br>AENCDKSLHTLFGDKLCTVATLRETYGEMADCCAKQEPE<br>RNECFLQHKDDNPNLPRLVRPEVDVMCTAFHDNEETFLK<br>KYLYEIARRHPYFYAPELLFFAKRYKAAFTECCQAADKAAC<br>LLPKLDELRDEGKASSAKQRLKCASLQKFGERAFKAWAVA<br>RLSQRFPKAEFAEVSKLVTDLTKVHTECCHGDLLECADDR<br>ADLAKYICENQDSISSKLKECCEKPLLEKSHCIAEVENDEMP<br>ADLPSLAADFVESKDVCKNYAEAKDVFLGMFLYEYARRHP<br>DYSVVLLLRLAKTYETTLEKCCAAADPHECYAKVFDEFKPL<br>VEEPQNLIKQNCELFEQLGEYKFQNALLVRYTKKVPQVST<br>PTLVEVSRNLGKVGSKCCKHPEAKRMPCAEDYLSVVLNQ<br>LCVLHEKTPVSDRVTKCCTESLVNRRPCFSALEVDETYVPK<br>EFNAETFTFHADICTLSEKERQIKKQTALVELVKHKPKATK<br>EQLKAVMDDFAAFVEKCCKADDKETCFAEEGKKLVAAS<br>QAALGLESPKAQASSVPTAQPQAEGSLAKATTAPATTRN<br>TGRGGEEKKKEKEKEEQEERETKTPDCDIEGKDGKQYESV<br>LMVSIDQLLDSMKEIGSNCLNNEFNFFKRHICDANKEGM |

TABLE 4-continued

| Amino Acid Sequences for Representative IL-7 Fusion Proteins | |
|---|---|
| IL-7 Fusion Protein (Internal Reference) | Sequence |
| | FLFRAARKLRQFLKMNSTGDFDLHLLKVSEGTTILLNCTG QVKGRKPAALGEAQPTKSLEENKSLKEQKKLNDLCFLKRL LQEIKTCWNKILMGTKEH (SEQ ID NO: 20) |

Example 3: Pharmacokinetic Profiles of IL-7 Fusion Proteins

Figure 2:
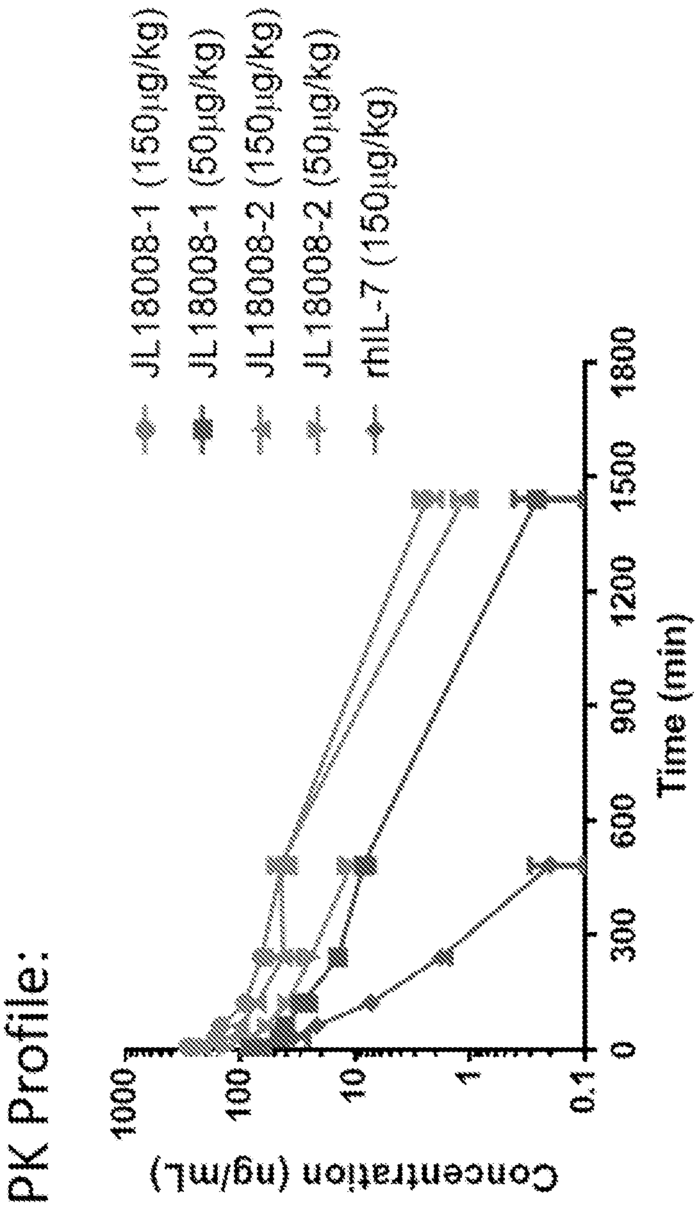
FIG. 2 illustrates the pharmacokinetic profiles of JL18008-1 (IL-7-HSA) and JL18008-2 (HSA-IL-7) fusion proteins.
Figure 3A:
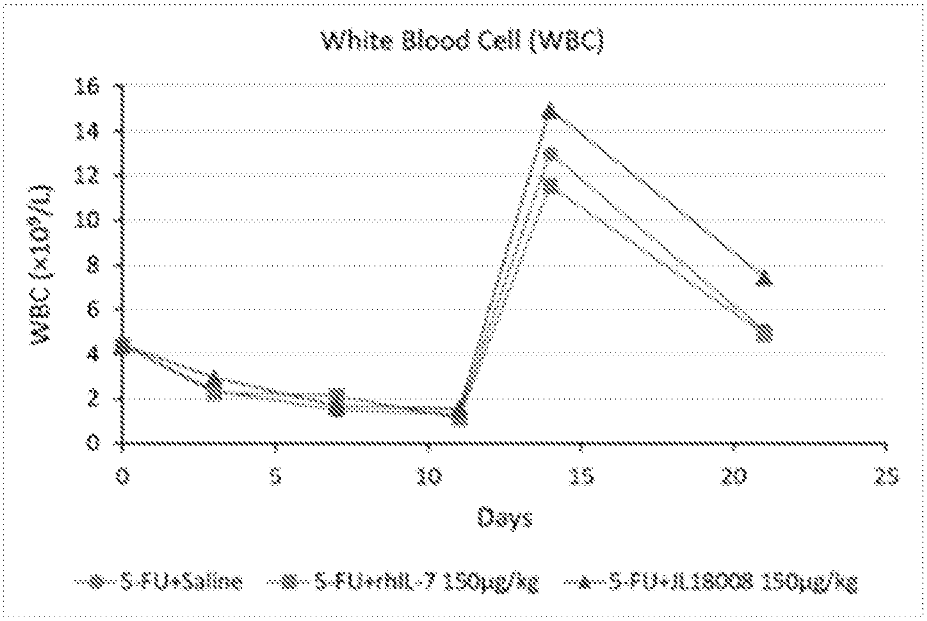
FIGS. 3A-3E illustrate recovery of immune cell populations following in vivo administration of JL18008-2 to lymphopenic mice.
Figure 3B:
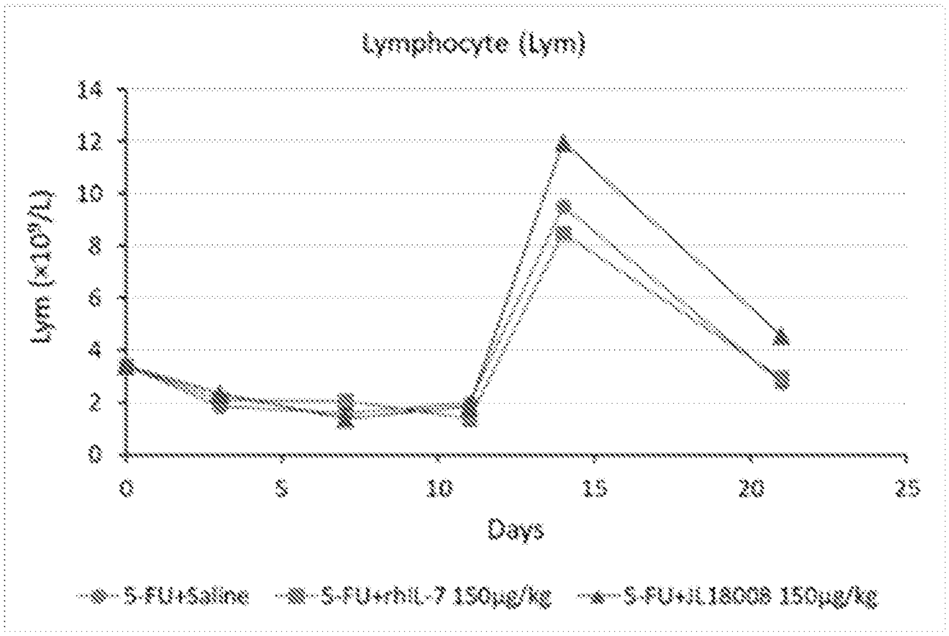
Figure 3C:
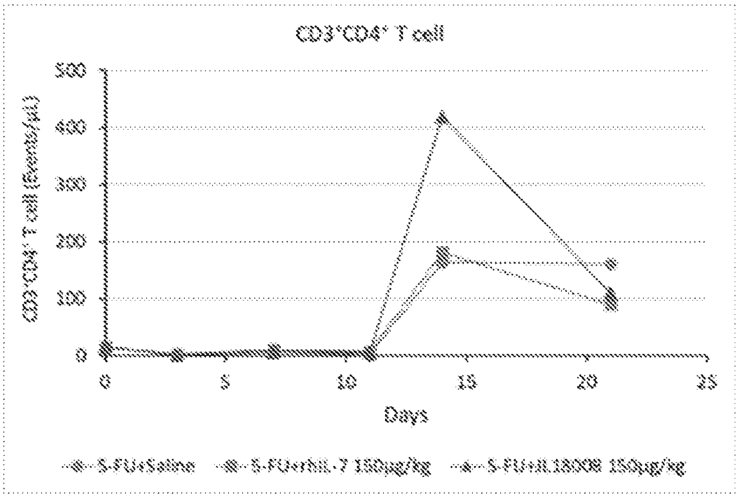
Figure 3D:
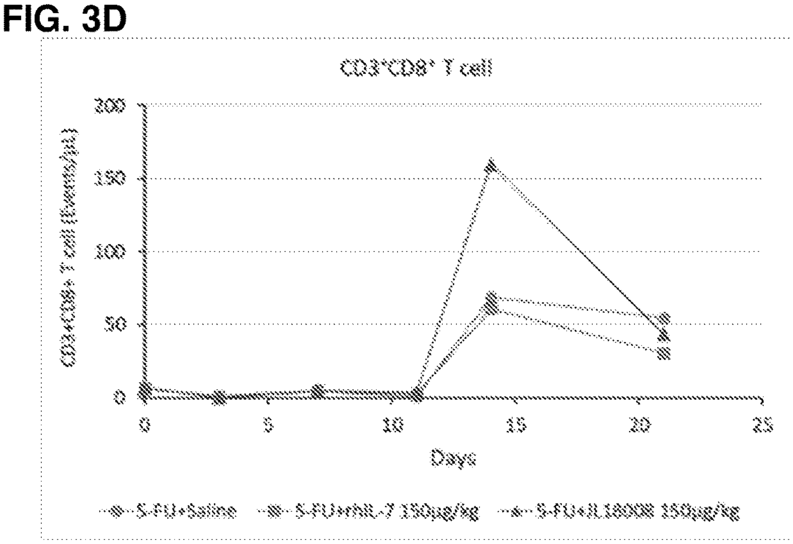
Figure 3E:
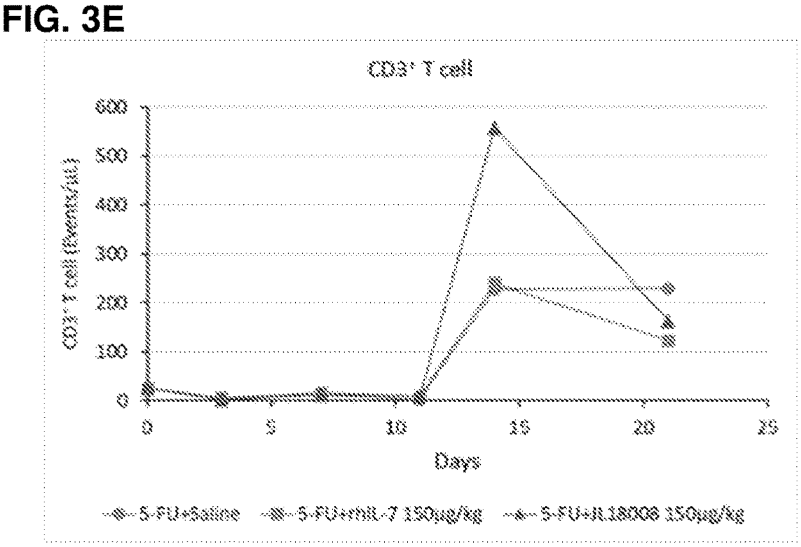

The pharmacokinetic (PK) profiles of JL18008-1 (IL-7-HSA) and JL18008-2 (HSA-IL-7) fusion proteins are examined. JL18008-1 and JL18008-2 are diluted in saline and administered intravenously to C57BL6/N mice at 50 μg/kg or 150 μg/kg. Recombinant human IL-7 (rhIL-7; Peprotech) is administered as a control at 150 μg/kg. Blood samples are obtained by retro-orbital bleeding at 5 min, 30 min, 1 hr, 2 hr, 4 hr, 8 hr, 24 hr, 72 hr, 96 hr, 120 hr, and 192 hr post-injection. The blood samples are centrifuged (5000 rpm) at 4° C. for 15 min to obtain serum. The concentration of human IL-7 (hIL-7) in JL18008-1, JL18008-2, and rhIL-7 serum samples are analyzed by Human IL-7 Quantikine HS ELISA Kit (R&D Systems, Cat #HS750), and PK values are calculated with PKSolver software. PK values are summarized in Table 5 and illustrated in FIG. 2.

TABLE 5

PK Profile of JL18008-1 and JL18008-2

| Sample | Dose (μg/kg) | $C_{max}$ (ng/mL) | $T_{max}$ (min) | $T_{1/2}$ (min) | $AUC_{0-t}$ (ng/ml * min) |
|---|---|---|---|---|---|
| JL18008-1 | 150 | 285.54 | 5 | 323.64 | 64790.32 |
| (IL-7-HSA) | 50 | 81.46 | 5 | 199.40 | 14758.73 |
| JL18008-2 | 150 | 203.69 | 5 | 220.55 | 52785.14 |
| (HSA-IL-7) | 50 | 134.04 | 5 | 195.83 | 16233.22 |
| rhIL-7 (PeproTech) | 150 | 76.33 | 5 | 68.56 | 4108.28 |

At 150 μg/kg, rhIL-7 exhibits a half-life of 68.56 min (~1.1 hour). At 50 μg/kg and 150 mg/kg, JL18008-1 exhibits a half-life of 323.54 min (5.4 hr) and 199.40 min (3.3 hr), respectively. At 50 μg/kg and 150 μg/kg, JL18008-2 exhibits a half-life of 220.55 min (3.7 hr) and 195.83 min (3.3 hr), respectively. These data demonstrate the IL-7 fusion proteins extend the half-life of hIL-7 as compared to control rhIL-7.

Example 4: Effect of JL18008-2 on Lymphopenic Mice

The efficacy of JL18008-2 (HSA-IL-7) is examined in vivo using a murine model of lymphopenia. Balb/C mice are injected intraperitoneally with 200 mg/kg of the chemotherapy drug 5-fluorouracil (5-FU) to induce lymphopenia at Day 0. Mice are injected with 150 μg/kg of JL18008-2 or rhIL-7 at Day 2, 4, and 6. Saline is injected as a negative control. Blood samples are obtained by retro-orbital bleeding, without centrifugation, at Day 0, 3, 7, 11, 14, and 21 and analyzed by flow cytometry. As illustrated in FIGS. 3A-3E, at Day 14 and 21, white blood cell (WBC) and lymphocyte (Lym) numbers are increased in the JL18008-2 treated mice as compared to those treated with rhIL-7 or the saline control. At Day 14, $CD3^+CD4^+$, $CD3^+CD8^+$, and $CD3^+$ T cell populations are significantly elevated in the JL18008-2 treated mice as compared to those treated with rhIL-7 or the saline control. Compared to the negative control, rhIL-7 did not show any effect of improved lymphocyte recovery, possibly due to its short in vivo half-life. These data demonstrate administration of JL18008-2 promotes recovery of white blood cells, lymphocytes, and T cell populations in lymphopenic mice, and suggests JL18008-2 can promote recovery of immune cell populations in lymphopenic subjects.

Example 5: Bioactivity of JL18008-2 In Vitro

Figure 4:
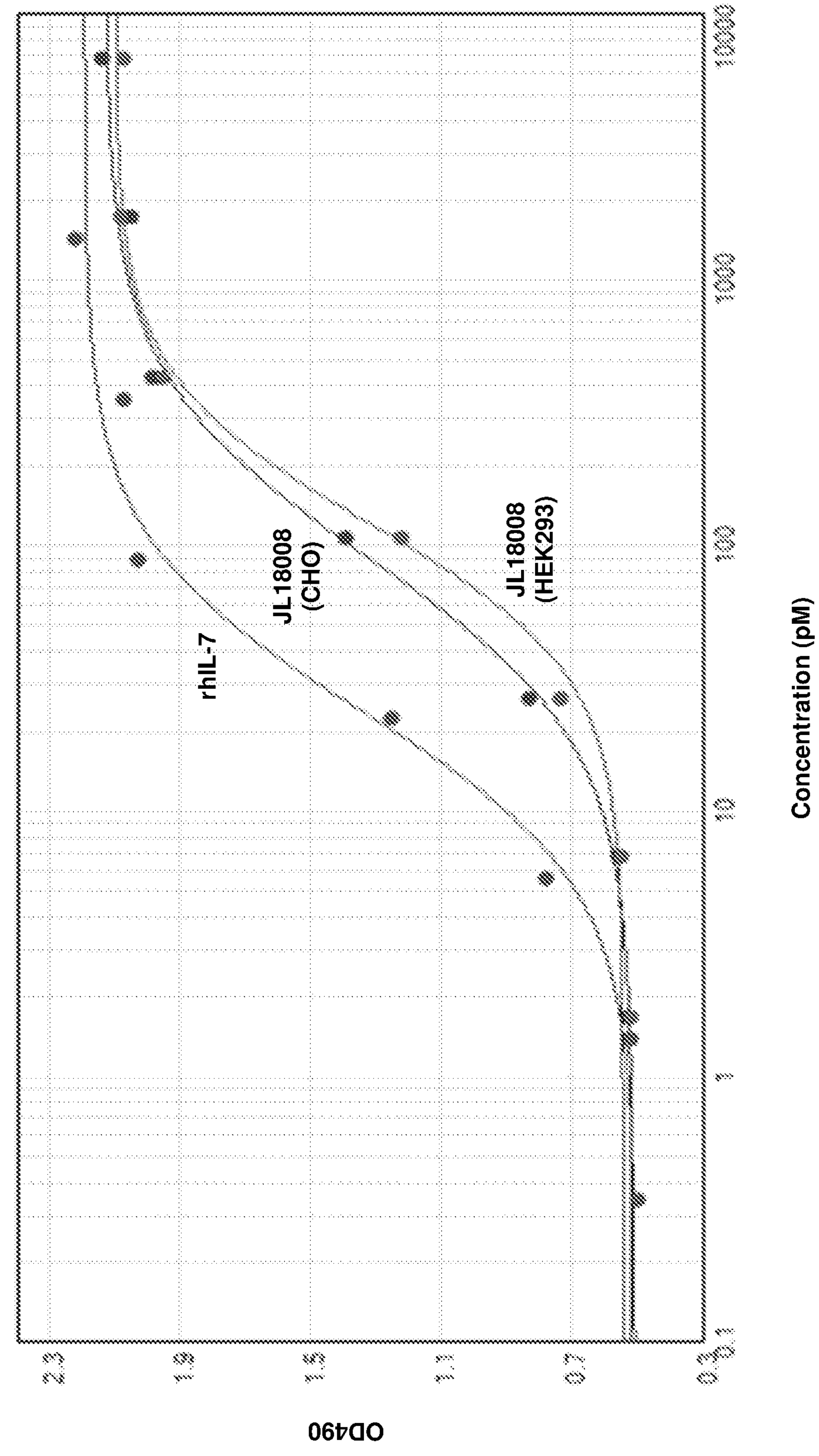
FIG. 4 illustrates the in vitro bioactivity of JL18008-2.

To investigate the bioactivity of JL18008-2 (HSA-IL-7), 2E8 cells (ATCC TIB-239), which are immature, murine B lymphocytes, were seeded into a 96-well plate ($5\times10^4$ cells/100 μL/well) and JL18008-2 isolated from CHO cells, JL18008-2 isolated from HEK293 cells, or rhIL-7 (Peprotech) were stepwise diluted and added to the wells (100 μL/well). The cells were incubated at 37° C., 5% $CO_2$ for 65 hours, treated with MTS at a concentration of 20 μL/well, and incubated 37° C., 5% $CO_2$ for 6 hours. The resulting absorbance was measured at 490 nm (FIG. 4). EC50 values of cell proliferation were obtained from plotting a dose response curve according to standard techniques. As illustrated in Table 6, the EC50 values of JL18008-2 were 4- to 6-fold higher than the EC50 value of rhIL-7. The lower in vitro activity of the IL-7 fusion proteins in FIG. 4 was likely due to steric hindrance.

TABLE 6

EC50 values of JL18008-2 and rhIL-7

| Sample | EC50 (pM) |
|---|---|
| JL18008-2 (CHO) | 89.7 |
| JL18008-2 (HEK293) | 121.1 |
| rhIL-7 | 24.1 |

We claim:

1. A fusion protein comprising:

a) an IL-7 protein;

b) a hinge region; and c) an albumin protein, wherein the hinge region covalently links the IL-7 protein and the albumin protein, and wherein the fusion protein comprises SEQ ID NO: 19.

2. The fusion protein of claim 1, wherein the serum half-life of the IL-7 is extended in the fusion protein relative to recombinant or exogenous human IL-7 by at least two hours when administered to a subject.

3. The fusion protein of claim 1, wherein the serum half-life of the IL-7 is extended in the fusion protein relative to recombinant or exogenous human IL-7 by at least four hours when administered to a subject.

4. The fusion protein of claim 2, wherein when the subject is administered the fusion protein in a range of 50-150 μg/kg, the serum half-life of the human IL-7 is 195-325 minutes.

5. A composition comprising the fusion protein of claim 1 and a pharmaceutically acceptable carrier, diluent, or excipient.

6. A kit comprising the fusion protein of claim 1 and a pharmaceutically acceptable carrier, diluent, or excipient.

7. A method for treating a subject having lymphopenia or immunodeficiency, comprising administering to the subject a composition comprising a fusion protein comprising human IL-7, a hinge region, and human serum albumin, wherein the hinge region covalently links the IL-7 protein and the albumin protein, and wherein the fusion protein comprises SEQ ID NO: 19.

8. The method of claim 7, wherein the subject has a disease or disorder selected from the group consisting of cancer, human immunodeficiency virus, hepatitis B, hepatitis C, lymphopenia, and sepsis.

9. The method of claim 7, wherein the subject has undergone stem cell transplantation.

10. A method for stimulating lymphocyte proliferation and lymphocyte differentiation, comprising administering to a subject in need of stimulation, a composition comprising a fusion protein comprising human IL-7, a hinge region, and human serum albumin, wherein the hinge region covalently links the IL-7 protein and the albumin protein, and wherein the fusion protein comprises SEQ ID NO: 19.

11. The method of claim 10, wherein the subject has undergone stem cell transplantation.

* * * * *

SEQUENCE LISTING

<160> NUMBER OF SEQ ID NOS: 20

<210> SEQ ID NO 1
<211> LENGTH: 36
<212> TYPE: DNA

```
<213> ORGANISM: Artificial
<220> FEATURE:
<223> OTHER INFORMATION: synthetic

<400> SEQUENCE: 1

gtgcctggca gcaccggaga ttgtgatatt gagggc                          36


<210> SEQ ID NO 2
<211> LENGTH: 39
<212> TYPE: DNA
<213> ORGANISM: Artificial
<220> FEATURE:
<223> OTHER INFORMATION: synthetic

<400> SEQUENCE: 2

gcctgggcct ttggggactc gtgttccttt gtgcccatc                       39


<210> SEQ ID NO 3
<211> LENGTH: 37
<212> TYPE: DNA
<213> ORGANISM: Artificial
<220> FEATURE:
<223> OTHER INFORMATION: synthetic

<400> SEQUENCE: 3

agagagacca agacaccaga ttgtgatatt gagggca                         37


<210> SEQ ID NO 4
<211> LENGTH: 47
<212> TYPE: DNA
<213> ORGANISM: Artificial
<220> FEATURE:
<223> OTHER INFORMATION: synthetic

<400> SEQUENCE: 4

acgggccctc tagactcgag tcatcagtgt tcctttgtgc ccatcag              47


<210> SEQ ID NO 5
<211> LENGTH: 37
<212> TYPE: DNA
<213> ORGANISM: Artificial Sequence
<220> FEATURE:
<223> OTHER INFORMATION: synthetic

<400> SEQUENCE: 5

agagagacca agacaccaga tgctcacaag tctgagg                         37


<210> SEQ ID NO 6
<211> LENGTH: 44
<212> TYPE: DNA
<213> ORGANISM: Artificial Sequence
<220> FEATURE:
<223> OTHER INFORMATION: synthetic

<400> SEQUENCE: 6

acgggccctc tagactcgag tcatcacagg cccagggcag cctg                 44


<210> SEQ ID NO 7
<211> LENGTH: 36
<212> TYPE: DNA
<213> ORGANISM: Artificial Sequence
<220> FEATURE:
<223> OTHER INFORMATION: synthetic

<400> SEQUENCE: 7

gtgcctggca gcaccggaga tgctcacaag tctgag                          36
```

<210> SEQ ID NO 8
<211> LENGTH: 38
<212> TYPE: DNA
<213> ORGANISM: Artificial Sequence
<220> FEATURE:
<223> OTHER INFORMATION: synthetic

<400> SEQUENCE: 8
gcctgggcct ttggggactc caggcccagg gcagcctg 38

<210> SEQ ID NO 9
<211> LENGTH: 27
<212> TYPE: DNA
<213> ORGANISM: Artificial Sequence
<220> FEATURE:
<223> OTHER INFORMATION: synthetic

<400> SEQUENCE: 9
cgtttaaact taagcttggt accgagc 27

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
tccggtgctg ccaggcaccc 20

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
gagtccccaa aggcccaggc 20

<210> SEQ ID NO 12
<211> LENGTH: 21
<212> TYPE: DNA
<213> ORGANISM: Artificial Sequence
<220> FEATURE:
<223> OTHER INFORMATION: sythetic

<400> SEQUENCE: 12
tggtgtcttg gtctctctct c 21

<210> SEQ ID NO 13
<211> LENGTH: 29
<212> TYPE: DNA
<213> ORGANISM: Artificial Sequence
<220> FEATURE:
<223> OTHER INFORMATION: synthetic

<400> SEQUENCE: 13
cgcgcgacgc gtggctccgg tgcccgtca 29

<210> SEQ ID NO 14
<211> LENGTH: 36
<212> TYPE: DNA
<213> ORGANISM: Artificial Sequence
<220> FEATURE:

<223> OTHER INFORMATION: synthetic

<400> SEQUENCE: 14
ctactagcta gctcacgaca cctgaaatgg aagaaa 36

<210> SEQ ID NO 15
<211> LENGTH: 152
<212> TYPE: PRT
<213> ORGANISM: Artificial Sequence
<220> FEATURE:
<223> OTHER INFORMATION: synthetic

<400> SEQUENCE: 15

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 16
<211> LENGTH: 585
<212> TYPE: PRT
<213> ORGANISM: Artificial Sequence
<220> FEATURE:
<223> OTHER INFORMATION: synthetic

<400> SEQUENCE: 16

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125
```

-continued

```
Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540
```

Lys Ala Val Met Asp Asp Phe Ala Ala Phe Val Glu Lys Cys Cys Lys
545 550 555 560

Ala Asp Asp Lys Glu Thr Cys Phe Ala Glu Glu Gly Lys Lys Leu Val
565 570 575

Ala Ala Ser Gln Ala Ala Leu Gly Leu
580 585

<210> SEQ ID NO 17
<211> LENGTH: 20
<212> TYPE: PRT
<213> ORGANISM: Artificial Sequence
<220> FEATURE:
<223> OTHER INFORMATION: synthetic

<400> SEQUENCE: 17

Met Glu Thr Asp Thr Leu Leu Leu Trp Val Leu Leu Leu Trp Val Pro
1 5 10 15

Gly Ser Thr Gly
20

<210> SEQ ID NO 18
<211> LENGTH: 58
<212> TYPE: PRT
<213> ORGANISM: Artificial Sequence
<220> FEATURE:
<223> OTHER INFORMATION: synthetic

<400> SEQUENCE: 18

Glu Ser Pro Lys Ala Gln Ala Ser Ser Val Pro Thr Ala Gln Pro Gln
1 5 10 15

Ala Glu Gly Ser Leu Ala Lys Ala Thr Thr Ala Pro Ala Thr Thr Arg
20 25 30

Asn Thr Gly Arg Gly Gly Glu Glu Lys Lys Lys Glu Lys Glu Lys Glu
35 40 45

Glu Gln Glu Glu Arg Glu Thr Lys Thr Pro
50 55

<210> SEQ ID NO 19
<211> LENGTH: 812
<212> TYPE: PRT
<213> ORGANISM: Artificial Sequence
<220> FEATURE:
<223> OTHER INFORMATION: synthetic

<400> SEQUENCE: 19

Met Glu Thr Asp Thr Leu Leu Leu Trp Val Leu Leu Leu Trp Val Pro
1 5 10 15

Gly Ser Thr Gly Asp Cys Asp Ile Glu Gly Lys Asp Gly Lys Gln Tyr
20 25 30

Glu Ser Val Leu Met Val Ser Ile Asp Gln Leu Leu Asp Ser Met Lys
35 40 45

Glu Ile Gly Ser Asn Cys Leu Asn Asn Glu Phe Asn Phe Phe Lys Arg
50 55 60

His Ile Cys Asp Ala Asn Lys Glu Gly Met Phe Leu Phe Arg Ala Ala
65 70 75 80

Arg Lys Leu Arg Gln Phe Leu Lys Met Asn Ser Thr Gly Asp Phe Asp
85 90 95

Leu His Leu Leu Lys Val Ser Glu Gly Thr Thr Ile Leu Leu Asn Cys
100 105 110

-continued

Thr Gly Gln Val Lys Gly Arg Lys Pro Ala Ala Leu Gly Glu Ala Gln
115 120 125

Pro Thr Lys Ser Leu Glu Glu Asn Lys Ser Leu Lys Glu Gln Lys Lys
130 135 140

Leu Asn Asp Leu Cys Phe Leu Lys Arg Leu Leu Gln Glu Ile Lys Thr
145 150 155 160

Cys Trp Asn Lys Ile Leu Met Gly Thr Lys Glu His Glu Ser Pro Lys
165 170 175

Ala Gln Ala Ser Ser Val Pro Thr Ala Gln Pro Gln Ala Glu Gly Ser
180 185 190

Leu Ala Lys Ala Thr Thr Ala Pro Ala Thr Thr Arg Asn Thr Gly Arg
195 200 205

Gly Gly Glu Glu Lys Lys Lys Glu Lys Glu Lys Glu Glu Gln Glu Glu
210 215 220

Arg Glu Thr Lys Thr Pro Asp Ala His Lys Ser Glu Val Ala His Arg
225 230 235 240

Phe Lys Asp Leu Gly Glu Glu Asn Phe Lys Ala Leu Val Leu Ile Ala
245 250 255

Phe Ala Gln Tyr Leu Gln Gln Cys Pro Phe Glu Asp His Val Lys Leu
260 265 270

Val Asn Glu Val Thr Glu Phe Ala Lys Thr Cys Val Ala Asp Glu Ser
275 280 285

Ala Glu Asn Cys Asp Lys Ser Leu His Thr Leu Phe Gly Asp Lys Leu
290 295 300

Cys Thr Val Ala Thr Leu Arg Glu Thr Tyr Gly Glu Met Ala Asp Cys
305 310 315 320

Cys Ala Lys Gln Glu Pro Glu Arg Asn Glu Cys Phe Leu Gln His Lys
325 330 335

Asp Asp Asn Pro Asn Leu Pro Arg Leu Val Arg Pro Glu Val Asp Val
340 345 350

Met Cys Thr Ala Phe His Asp Asn Glu Glu Thr Phe Leu Lys Lys Tyr
355 360 365

Leu Tyr Glu Ile Ala Arg Arg His Pro Tyr Phe Tyr Ala Pro Glu Leu
370 375 380

Leu Phe Phe Ala Lys Arg Tyr Lys Ala Ala Phe Thr Glu Cys Cys Gln
385 390 395 400

Ala Ala Asp Lys Ala Ala Cys Leu Leu Pro Lys Leu Asp Glu Leu Arg
405 410 415

Asp Glu Gly Lys Ala Ser Ser Ala Lys Gln Arg Leu Lys Cys Ala Ser
420 425 430

Leu Gln Lys Phe Gly Glu Arg Ala Phe Lys Ala Trp Ala Val Ala Arg
435 440 445

Leu Ser Gln Arg Phe Pro Lys Ala Glu Phe Ala Glu Val Ser Lys Leu
450 455 460

Val Thr Asp Leu Thr Lys Val His Thr Glu Cys Cys His Gly Asp Leu
465 470 475 480

Leu Glu Cys Ala Asp Asp Arg Ala Asp Leu Ala Lys Tyr Ile Cys Glu
485 490 495

Asn Gln Asp Ser Ile Ser Ser Lys Leu Lys Glu Cys Cys Glu Lys Pro
500 505 510

Leu Leu Glu Lys Ser His Cys Ile Ala Glu Val Glu Asn Asp Glu Met
515 520 525

-continued

```
Pro Ala Asp Leu Pro Ser Leu Ala Ala Asp Phe Val Glu Ser Lys Asp
    530                 535                 540

Val Cys Lys Asn Tyr Ala Glu Ala Lys Asp Val Phe Leu Gly Met Phe
545                 550                 555                 560

Leu Tyr Glu Tyr Ala Arg Arg His Pro Asp Tyr Ser Val Val Leu Leu
                565                 570                 575

Leu Arg Leu Ala Lys Thr Tyr Glu Thr Thr Leu Glu Lys Cys Cys Ala
            580                 585                 590

Ala Ala Asp Pro His Glu Cys Tyr Ala Lys Val Phe Asp Glu Phe Lys
        595                 600                 605

Pro Leu Val Glu Asn Leu Ile Lys Gln Asn Cys Glu Leu Phe Glu Gln
    610                 615                 620

Leu Gly Glu Tyr Lys Phe Gln Asn Ala Leu Leu Val Arg Tyr Thr Lys
625                 630                 635                 640

Lys Val Pro Gln Val Ser Thr Pro Thr Leu Val Glu Val Ser Arg Asn
                645                 650                 655

Leu Gly Lys Val Gly Ser Lys Cys Cys Lys His Pro Glu Ala Lys Arg
            660                 665                 670

Met Pro Cys Ala Glu Asp Tyr Leu Ser Val Val Leu Asn Gln Leu Cys
        675                 680                 685

Val Leu His Glu Lys Thr Pro Val Ser Asp Arg Val Thr Lys Cys Cys
    690                 695                 700

Thr Glu Ser Leu Val Asn Arg Arg Pro Cys Phe Ser Ala Leu Glu Val
705                 710                 715                 720

Asp Glu Thr Tyr Val Pro Lys Glu Phe Asn Ala Glu Thr Phe Thr Phe
                725                 730                 735

His Ala Asp Ile Cys Thr Leu Ser Glu Lys Glu Arg Gln Ile Lys Lys
            740                 745                 750

Gln Thr Ala Leu Val Glu Leu Val Lys His Lys Pro Lys Ala Thr Lys
        755                 760                 765

Glu Gln Leu Lys Ala Val Met Asp Asp Phe Ala Ala Phe Val Glu Lys
    770                 775                 780

Cys Cys Lys Ala Asp Asp Lys Glu Thr Cys Phe Ala Glu Glu Gly Lys
785                 790                 795                 800

Lys Leu Val Ala Ala Ser Gln Ala Ala Leu Gly Leu
                805                 810


<210> SEQ ID NO 20
<211> LENGTH: 815
<212> TYPE: PRT
<213> ORGANISM: Artificial Sequence
<220> FEATURE:
<223> OTHER INFORMATION: synthetic

<400> SEQUENCE: 20

Met Glu Thr Asp Thr Leu Leu Leu Trp Val Leu Leu Leu Trp Val Pro
1               5                   10                  15

Gly Ser Thr Gly Asp Ala His Lys Ser Glu Val Ala His Arg Phe Lys
            20                  25                  30

Asp Leu Gly Glu Glu Asn Phe Lys Ala Leu Val Leu Ile Ala Phe Ala
        35                  40                  45

Gln Tyr Leu Gln Gln Cys Pro Phe Glu Asp His Val Lys Leu Val Asn
    50                  55                  60

Glu Val Thr Glu Phe Ala Lys Thr Cys Val Ala Asp Glu Ser Ala Glu
65                  70                  75                  80
```

-continued

```
Asn Cys Asp Lys Ser Leu His Thr Leu Phe Gly Asp Lys Leu Cys Thr
                85                  90                  95

Val Ala Thr Leu Arg Glu Thr Tyr Gly Glu Met Ala Asp Cys Cys Ala
            100                 105                 110

Lys Gln Glu Pro Glu Arg Asn Glu Cys Phe Leu Gln His Lys Asp Asp
        115                 120                 125

Asn Pro Asn Leu Pro Arg Leu Val Arg Pro Glu Val Asp Val Met Cys
    130                 135                 140

Thr Ala Phe His Asp Asn Glu Glu Thr Phe Leu Lys Lys Tyr Leu Tyr
145                 150                 155                 160

Glu Ile Ala Arg Arg His Pro Tyr Phe Tyr Ala Pro Glu Leu Leu Phe
                165                 170                 175

Phe Ala Lys Arg Tyr Lys Ala Ala Phe Thr Glu Cys Cys Gln Ala Ala
            180                 185                 190

Asp Lys Ala Ala Cys Leu Leu Pro Lys Leu Asp Glu Leu Arg Asp Glu
        195                 200                 205

Gly Lys Ala Ser Ser Ala Lys Gln Arg Leu Lys Cys Ala Ser Leu Gln
    210                 215                 220

Lys Phe Gly Glu Arg Ala Phe Lys Ala Trp Ala Val Ala Arg Leu Ser
225                 230                 235                 240

Gln Arg Phe Pro Lys Ala Glu Phe Ala Glu Val Ser Lys Leu Val Thr
                245                 250                 255

Asp Leu Thr Lys Val His Thr Glu Cys Cys His Gly Asp Leu Leu Glu
            260                 265                 270

Cys Ala Asp Asp Arg Ala Asp Leu Ala Lys Tyr Ile Cys Glu Asn Gln
        275                 280                 285

Asp Ser Ile Ser Ser Lys Leu Lys Glu Cys Cys Glu Lys Pro Leu Leu
    290                 295                 300

Glu Lys Ser His Cys Ile Ala Glu Val Glu Asn Asp Glu Met Pro Ala
305                 310                 315                 320

Asp Leu Pro Ser Leu Ala Ala Asp Phe Val Glu Ser Lys Asp Val Cys
                325                 330                 335

Lys Asn Tyr Ala Glu Ala Lys Asp Val Phe Leu Gly Met Phe Leu Tyr
            340                 345                 350

Glu Tyr Ala Arg Arg His Pro Asp Tyr Ser Val Val Leu Leu Leu Arg
        355                 360                 365

Leu Ala Lys Thr Tyr Glu Thr Thr Leu Glu Lys Cys Cys Ala Ala Ala
    370                 375                 380

Asp Pro His Glu Cys Tyr Ala Lys Val Phe Asp Glu Phe Lys Pro Leu
385                 390                 395                 400

Val Glu Glu Pro Gln Asn Leu Ile Lys Gln Asn Cys Glu Leu Phe Glu
                405                 410                 415

Gln Leu Gly Glu Tyr Lys Phe Gln Asn Ala Leu Leu Val Arg Tyr Thr
            420                 425                 430

Lys Lys Val Pro Gln Val Ser Thr Pro Thr Leu Val Glu Val Ser Arg
        435                 440                 445

Asn Leu Gly Lys Val Gly Ser Lys Cys Cys Lys His Pro Glu Ala Lys
    450                 455                 460

Arg Met Pro Cys Ala Glu Asp Tyr Leu Ser Val Val Leu Asn Gln Leu
465                 470                 475                 480

Cys Val Leu His Glu Lys Thr Pro Val Ser Asp Arg Val Thr Lys Cys
                485                 490                 495
```

-continued

```
Cys Thr Glu Ser Leu Val Asn Arg Arg Pro Cys Phe Ser Ala Leu Glu
            500                 505                 510

Val Asp Glu Thr Tyr Val Pro Lys Glu Phe Asn Ala Glu Thr Phe Thr
        515                 520                 525

Phe His Ala Asp Ile Cys Thr Leu Ser Glu Lys Glu Arg Gln Ile Lys
    530                 535                 540

Lys Gln Thr Ala Leu Val Glu Leu Val Lys His Lys Pro Lys Ala Thr
545                 550                 555                 560

Lys Glu Gln Leu Lys Ala Val Met Asp Asp Phe Ala Ala Phe Val Glu
                565                 570                 575

Lys Cys Cys Lys Ala Asp Asp Lys Glu Thr Cys Phe Ala Glu Glu Gly
            580                 585                 590

Lys Lys Leu Val Ala Ala Ser Gln Ala Ala Leu Gly Leu Glu Ser Pro
        595                 600                 605

Lys Ala Gln Ala Ser Ser Val Pro Thr Ala Gln Pro Gln Ala Glu Gly
    610                 615                 620

Ser Leu Ala Lys Ala Thr Thr Ala Pro Ala Thr Thr Arg Asn Thr Gly
625                 630                 635                 640

Arg Gly Gly Glu Glu Lys Lys Lys Glu Lys Glu Lys Glu Glu Gln Glu
                645                 650                 655

Glu Arg Glu Thr Lys Thr Pro Asp Cys Asp Ile Glu Gly Lys Asp Gly
            660                 665                 670

Lys Gln Tyr Glu Ser Val Leu Met Val Ser Ile Asp Gln Leu Leu Asp
        675                 680                 685

Ser Met Lys Glu Ile Gly Ser Asn Cys Leu Asn Asn Glu Phe Asn Phe
    690                 695                 700

Phe Lys Arg His Ile Cys Asp Ala Asn Lys Glu Gly Met Phe Leu Phe
705                 710                 715                 720

Arg Ala Ala Arg Lys Leu Arg Gln Phe Leu Lys Met Asn Ser Thr Gly
                725                 730                 735

Asp Phe Asp Leu His Leu Leu Lys Val Ser Glu Gly Thr Thr Ile Leu
            740                 745                 750

Leu Asn Cys Thr Gly Gln Val Lys Gly Arg Lys Pro Ala Ala Leu Gly
        755                 760                 765

Glu Ala Gln Pro Thr Lys Ser Leu Glu Glu Asn Lys Ser Leu Lys Glu
    770                 775                 780

Gln Lys Lys Leu Asn Asp Leu Cys Phe Leu Lys Arg Leu Leu Gln Glu
785                 790                 795                 800

Ile Lys Thr Cys Trp Asn Lys Ile Leu Met Gly Thr Lys Glu His
                805                 810                 815
```